(12) United States Patent
Nelson et al.

(10) Patent No.: US 7,727,722 B2
(45) Date of Patent: *Jun. 1, 2010

(54) LIGATION AMPLIFICATION

(75) Inventors: John Richard Nelson, Clifton Park, NY (US); Robert Scott Duthie, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 595 days.

This patent is subject to a terminal disclaimer.

(21) Appl. No.: 11/620,804

(22) Filed: Jan. 8, 2007

(65) Prior Publication Data

US 2009/0081644 A1 Mar. 26, 2009

Related U.S. Application Data

(63) Continuation-in-part of application No. 10/358,818, filed on Feb. 5, 2003, now Pat. No. 7,223,541, which is a continuation-in-part of application No. 10/113,030, filed on Apr. 1, 2002, now Pat. No. 7,052,839.

(60) Provisional application No. 60/315,798, filed on Aug. 29, 2001, provisional application No. 60/638,937, filed on Dec. 23, 2004, provisional application No. 60/685,661, filed on May 27, 2005.

(51) Int. Cl.
*C12Q 1/68* (2006.01)
(52) U.S. Cl. .......................... 435/6; 435/91.1; 435/91.2
(58) Field of Classification Search ........................ None
See application file for complete search history.

(56) References Cited

U.S. PATENT DOCUMENTS

| | | | |
|---|---|---|---|
| 5,194,370 | A | 3/1993 | Berninger et al. |
| 5,215,899 | A | 6/1993 | Dattagupta |
| 5,545,522 | A | 8/1996 | van Gelder et al. |
| 5,716,785 | A | 2/1998 | van Gelder et al. |
| 5,891,636 | A | 4/1999 | Van Gelder et al. |
| 5,914,229 | A | 6/1999 | Loewy |
| 2002/0187500 | A1 | 12/2002 | Laayoun |
| 2003/0064366 | A1* | 4/2003 | Hardin et al. .................. 435/6 |
| 2003/0077610 | A1 | 4/2003 | Nelson et al. |
| 2003/0096253 | A1 | 5/2003 | Nelson et al. |
| 2003/0162213 | A1 | 8/2003 | Fuller et al. |
| 2004/0152104 | A1 | 8/2004 | Sood et al. |

FOREIGN PATENT DOCUMENTS

| | | |
|---|---|---|
| EP | 369775 A2 * | 5/1990 |
| WO | WO 99/43850 | 9/1999 |
| WO | WO 03/020734 | 3/2003 |
| WO | WO03020984 | 3/2003 |
| WO | WO 2006/071776 | 7/2006 |
| WO | WO2006071776 | 7/2006 |

OTHER PUBLICATIONS

Sekiguchi et al. Biochemistry vol. 36:9073-9079. 1997.*
PCT Search Report—Jun. 18, 2008.
Sood et al., "Terminal Phosphate-Labeled Nucleotides with Improved Substrate Properties for Homogeneous Nucleic Acid Assays", Journal of the American Chemical Society, vol. 127, pp. 2394-2395 (2005).
Sekiguchi et al., "Ligation of RNA-Containing Deplexes by Vaccinia DNA Ligase", Biochemistry, vol. 36, pp. 9073-9079 (1997).
Fareed et al., "Enzymatic Breakage and Joining of Deoxyribonucleic Acid VIII. Hybrids of Ribo- and Deoxyribonucleotide Homopolymers as Substrates for Polynucleotide Ligase of Bacteriophage T4", Journal of Biological Chemistry, vol. 246, pp. 925-932 (1971).
Nath et al., "Covalent Attachment of Polyribonucleotides to Polydeoxyribonucleotides Catalyzed by Deoxyribonucleic Acid Ligase", Journal of Biological Chemistry, vol. 249, pp. 3680-3688 (1974).
Lopez et al., "The Low Processivity of T7 RNA Polymerase Over the Initially Transcribed Sequence can Limit Productive Initiation in Vivo", Journal of Molecular Biology, vol. 269, pp. 41-51 (1997).
Arnaud-Barbe et al., "Transcription of RNA templates by T7 RNA polymerase", Nucleic Acids Research, vol. 26, pp. 3550-3554 (1998).
Ling et al., "Abortive initiation by bacteriophage T3 and T7 RNA polymerases under conditions", Nucleic Acids Research, vol. 17, pp. 1605-1618 (1989).
Macdonald et al., "Termination and Slippage by Bacteriophage T7 Polymerase", Journal of Molecular Biology, vol. 232, pp. 1030-1047 (1993).

* cited by examiner

*Primary Examiner*—Heather G Calamita
(74) *Attorney, Agent, or Firm*—Eileen B. Gallagher

(57) ABSTRACT

Provided herein are methods and agents for ligation-based exponential ribonucleic acid amplification followed by detection using a nucleic acid polymerization reaction employing terminal-phosphate-labeled nucleotides including three or more phosphates as substrates for nucleic acid polymerase.

25 Claims, 7 Drawing Sheets

SEQUENCE LISTING

```
<160> NUMBER OF SEQ ID NOS: 11

<210> SEQ ID NO 1
<211> LENGTH: 47
<212> TYPE: DNA
<213> ORGANISM: Unknown
<220> FEATURE:
<223> OTHER INFORMATION: TAATACGACTCACTATA is a promoter sequence for
      T7 RNA polymerase, GGGAG is an intervening sequence (IVS), and
      24 base poly(dT) sequence hybridises with mRNA.

<400> SEQUENCE: 1
gtaatacgac tcactatagg gagtttttt ttttttttt ttttttt                    47
```

```
<210> SEQ ID NO 2
<211> LENGTH: 27
<212> TYPE: DNA
<213> ORGANISM: unknown
<220> FEATURE:
<223> OTHER INFORMATION: 5' phosphate group participates in covalent
      bond formation with the 3' hydroxyl group of mRNA. Four dA
      residues promote hybridizatioin of the 3' poly(rA) tail of mRNA.
      TATAGTGAGTCGTATTA is complementary to the promoter sequence.

<400> SEQUENCE: 2
aaaactccct atagtgagtc gtattac                                        27

<210> SEQ ID NO 3
<211> LENGTH: 60
<212> TYPE: DNA
<213> ORGANISM: unknown
<220> FEATURE:
<223> OTHER INFORMATION: TAATACGACTCACTATA is a promoter sequence for 17
      RNA polymerase. GGGAGACCACAACGG is a fifteen base intervening
      sequence. Twenty four base poly(dT) sequence hybridizes with polyA
      tail.

<400> SEQUENCE: 3
aaattaatac gactcactat agggagacca caacggtttt tttttttttt tttttttttt    60

<210> SEQ ID NO 4
<211> LENGTH: 39
<212> TYPE: DNA
<213> ORGANISM: unknown
<220> FEATURE:
<223> OTHER INFORMATION: The 5' phosphate group makes covalent bond with
      the 3' hydroxyl group of mRNA. Four dA residues  promote
      complementary binding of the 3' poly(rA) tail of mRNA.
      TATAGTGAGTCGTATTAA is complementary to promoter sequence.

<400> SEQUENCE: 4
aaaaccgttg tggtctccta tagtgagtcg tattaattt                           39

<210> SEQ ID NO 5
<211> LENGTH: 35
<212> TYPE: RNA
<213> ORGANISM: Artificial Sequence
<220> FEATURE:
<223> OTHER INFORMATION: A synthetic RNA designed to test ligation and
      transcription reactions.

<400> SEQUENCE: 5
uguuguuuuu uuuuuuuuuu uuuuuuuuuu uuuuu                               35

<210> SEQ ID NO 6
<211> LENGTH: 65
<212> TYPE: RNA
<213> ORGANISM: Artificial Sequence
<220> FEATURE:
<223> OTHER INFORMATION: A synthetic RNA designed to test ligation and
      transcription reactions.

<400> SEQUENCE: 6
uacaacgucg ugacugggaa aacaaaaaaa aaaaaaaaaa aaaaaaaaaa aaaaaaaaaa    60
aaaaa                                                                65

<210> SEQ ID NO 7
<211> LENGTH: 60
<212> TYPE: DNA
<213> ORGANISM: unknown
<220> FEATURE:
<223> OTHER INFORMATION: AATTAACCCTCACTAAA is a promoter sequence for
```

-continued

T3 RNA polymerase. GGGAGACCACAACGG is a 15 base intervening
sequence. 24 base poly(dT) sequence) is used to capture the mRNA.

<400> SEQUENCE: 7
aaataattaa ccctcactaa agggagacca caacggtttt tttttttttt tttttttttt      60

<210> SEQ ID NO 8
<211> LENGTH: 40
<212> TYPE: DNA
<213> ORGANISM: unknown
<220> FEATURE:
<223> OTHER INFORMATION: 5' phosphate group makes covalent bond with the
      3' hydroxyl group of mRNA. Four dA residues promote hybridizatioin
      of the 3' poly(rA) tail of mRNA. TTTAGTGAGGGTTAATT is
      complementary to the promoter sequence.

<400> SEQUENCE: 8
aaaaccgttg tggtctccct ttagtgaggg ttaattattt                            40

<210> SEQ ID NO 9
<211> LENGTH: 5
<212> TYPE: DNA
<213> ORGANISM: Artificial Sequence
<220> FEATURE:
<223> OTHER INFORMATION: The oligo is a primer for DNA synthesis and is
      an artificial sequence.

<400> SEQUENCE: 9 atccg                                                                  5

<210> SEQ ID NO 10
<211> LENGTH: 10
<212> TYPE: DNA
<213> ORGANISM: Artificial Sequence
<220> FEATURE:
<223> OTHER INFORMATION: The oligo is a template for DNA synthesis and
      is an artificial sequence.

<400> SEQUENCE: 10
taggccgctg                                                             10

<210> SEQ ID NO 11
<211> LENGTH: 10
<212> TYPE: DNA
<213> ORGANISM: Artificial Sequence
<220> FEATURE:
<223> OTHER INFORMATION: The oligo is a template for DNA synthesis and
      is an artificial sequence.

<400> SEQUENCE: 11
taggctgctg                                                             10

LIGATION AMPLIFICATION

CROSS REFERENCE TO RELATED APPLICATIONS

This application is a continuation in part of U.S. patent application Ser. No. 10/358,818, filed Feb. 5, 2003 now U.S. Pat. No. 7,223,541 which is a continuation-in-part of U.S. patent application Ser. No. 10/113,030, filed Apr. 1, 2002 now U.S. Pat. No. 7,052,839, which claims priority to U.S. Provisional Application No. 60/315,798, filed Aug. 29, 2001, all entitled "Terminal-phosphate-labeled Nucleotides and Methods of Use"; and U.S. Patent Application No. 60/638,937, filed Dec. 23, 2004; which claims priority to U.S. Provisional Application No. 60/685,661, filed May 27, 2005; and international Patent Application No. PCT/US2005/046800, filed Dec. 22, 2005, entitled "Ligation-based RNA Amplification."

INCORPORATION BY REFERENCE

This application incorporates by reference the Sequence Listing contained on the two compact discs (Copy 1 and Copy 2) containing the following file:
File name: "196453-1. ST25.txt" created Apr. 19, 2007, which is 1.98 kb in size.

BACKGROUND

Various methods are known for amplifying and detecting specific analytes such as nucleic acids with specificity and sensitivity. Such methods generally require the amplification step to occur before the detection step. Amplifications methods include polymerase chain reaction (PCR) and reverse transcriptase polymerase chain reaction (RT-PCR), used for the amplification of deoxyribonucleic acid (DNA) and ribonucleic acid (RNA) respectively. And, detection methods for nucleic acids generally include the use of detectable labels, for example, fluorescent labels or radioactive labels coupled to enzymes or antibodies.

Many ribonucleic acid (RNA) amplification methods include multi step reactions, for example, conversion of RNA to complimentary DNA (cDNA) as one of the steps and require multiple enzymes and intermediate purification steps.

Additionally, amplifying and detecting methods require the separation of labeled starting materials from the labeled product, using, for example electrophoresis, or affinity separation techniques.

It would, therefore, be of benefit to provide a method for exponential RNA amplification and subsequent detection that overcomes some of the limitations of known techniques.

FIELD OF THE INVENTION

The present invention relates generally to methods for ligation-based exponential ribonucleic acid amplification followed by detection using a nucleic acid polymerization reaction employing terminal-phosphate-labeled nucleotides including three or more phosphates as substrates for nucleic acid polymerase. Also disclosed are the uses of the method for detection and identification of specific targets.

BRIEF DESCRIPTION

In some embodiments, the present invention provides methods for amplifying and detecting a target RNA sequence. The methods include the steps of amplifying the target RNA sequence to produce amplified RNA sequences, reacting the amplified RNA sequence with a nucleic acid polymerase in presence of at least one terminal-phosphate-labeled nucleotide to produce a labeled polyphosphate and detecting the labeled polyphosphate. In some embodiments, the labeled polyphosphate is further reacted with a phosphate to produce a detectable species. In some embodiments, the individual steps are performed simultaneously in a single reaction vessel.

In some embodiments, the present invention provides methods for detecting the presence of a target RNA sequence in a sample including the steps of (a) amplifying the target RNA sequence to produce amplified RNA sequences (b) conducting a nucleic acid polymerase reaction on the amplified RNA sequences in presence of at least one terminal-phosphate-labeled nucleotide comprising three or more phosphate groups in polyphosphate chain, which reaction results in the production of a labeled polyphosphate and (c) detecting the labeled polyphosphate. For amplification, the target RNA is first hybridized with a nucleic acid sequence that comprises a double stranded region comprising a promoter sequence for RNA polymerase, and a single stranded 3' terminal region capable of hybridizing to the target RNA sequence. Following hybridization, 5' end of the double stranded region of the nucleic acid sequence is ligated to the 3' end of the target RNA sequence to form a ligated sequence. The ligated sequence is then transcribed with a RNA polymerase to form an amplified antisense, complementary RNA sequences. In some embodiments, a second round of amplification is performed on the amplified antisense complementary RNA sequences to provide amplified sense RNA sequences.

In some embodiments, the present invention further provides a kit for simultaneous amplification and detection of a target RNA sequence in a sample. The kit includes at least one nucleic acid sequence comprising a double stranded region comprising a promoter sequence for RNA polymerase and a single stranded 3' terminal region capable of hybridizing to the target ribonucleic acid sequence; a ligation enzyme; nucleotides that are substantially resistant to phosphatases; at least one of DNA polymerase, RNA polymerase, an exonuclease, reverse transcriptase or combinations thereof; one or more terminal-phosphate-labeled nucleotide and a phosphatase. The recessed 5' end of the nucleic acid sequences is phosphorylated and the terminal 3' end is capped with a polymerase extension blocker. The ligation enzyme in the kit is capable of ligating the target RNA sequence to the nucleic acid sequence in presence of a cofactor that is substantially resistant to the phosphatase. Terminal-phosphate labeled nucleotide is of the formula:

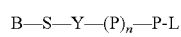

wherein P=phosphate ($PO_3$) and derivatives thereof, n is 2 or greater; Y is an oxygen or sulfur atom; B is a nitrogen-containing heterocyclic base; S is an acyclic moiety, carbocyclic moiety or sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P-L is a phosphorylated label which preferably becomes independently detectable when the phosphate is removed.

FIGURES

These and other features, aspects, and advantages of the present invention will become better understood when the following detailed description is read with reference to the accompanying figures.

DETAILED DESCRIPTION

Figure 1:
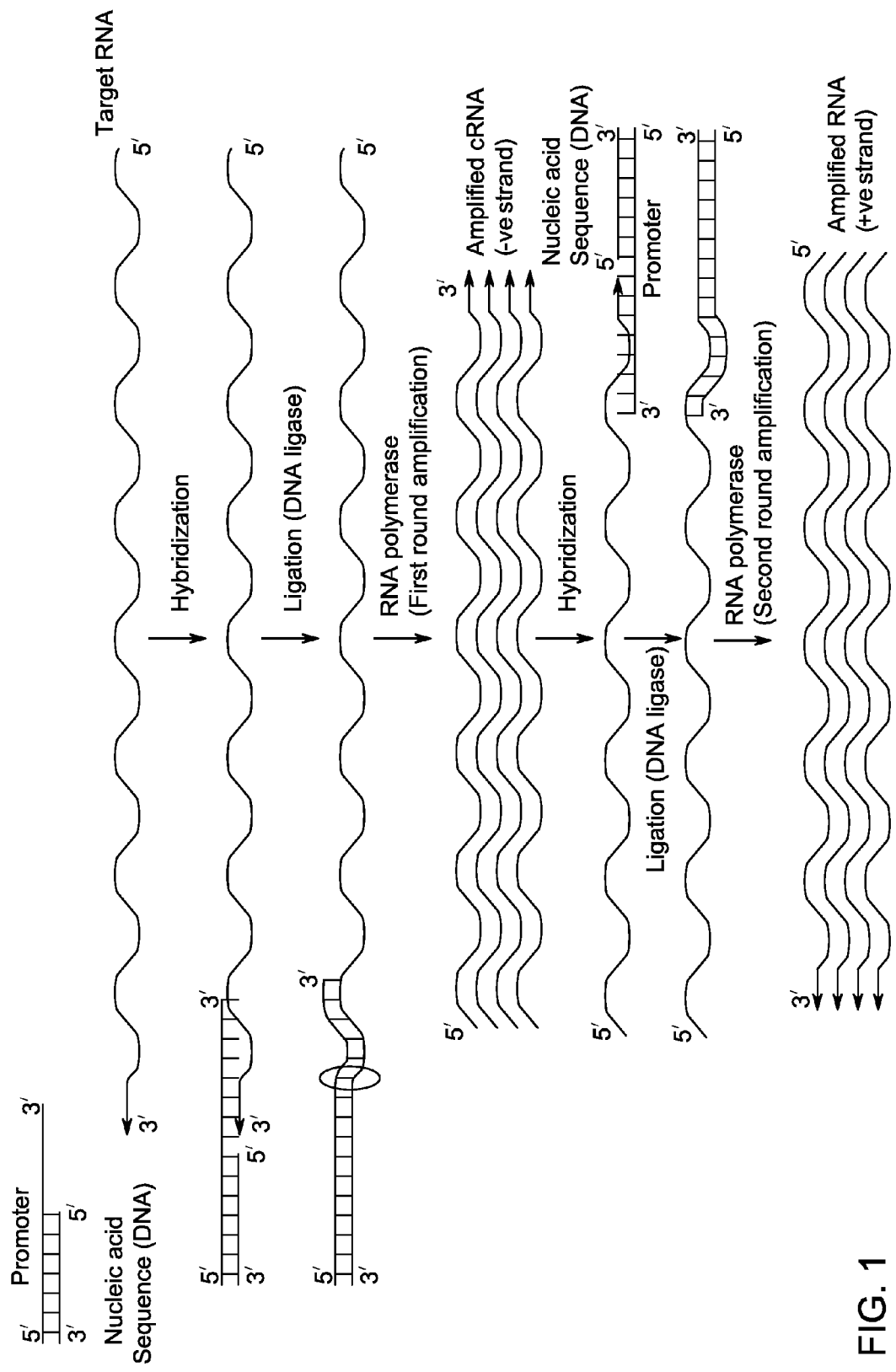
FIG. 1 is a schematic representation of exponential RNA amplification by initial ligation and subsequent transcription reactions
Figure 2:
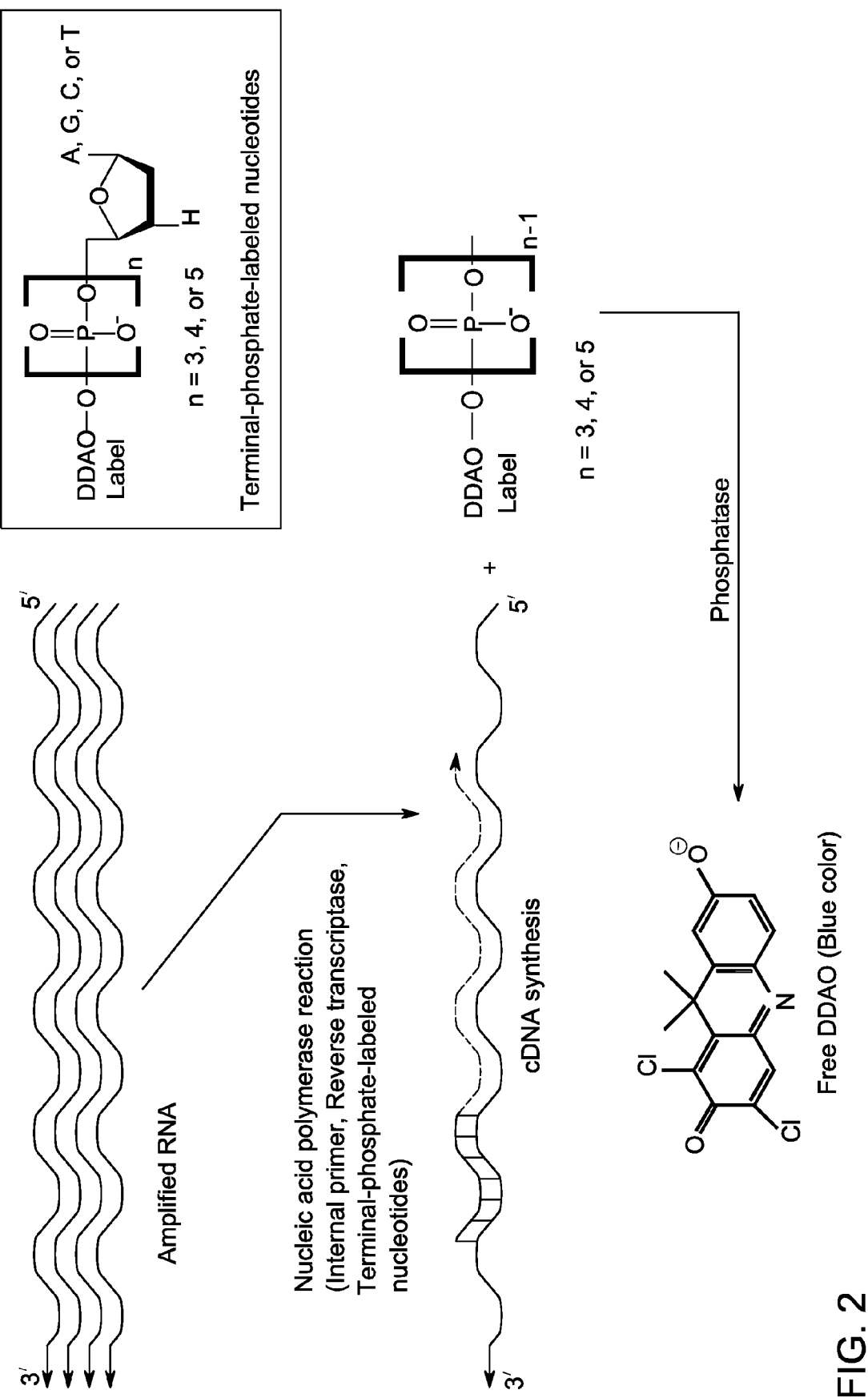
FIG. 2 is a schematic representation of detection of amplified RNA sequences using terminal-phosphate-labeled nucleotides.
Figure 3:
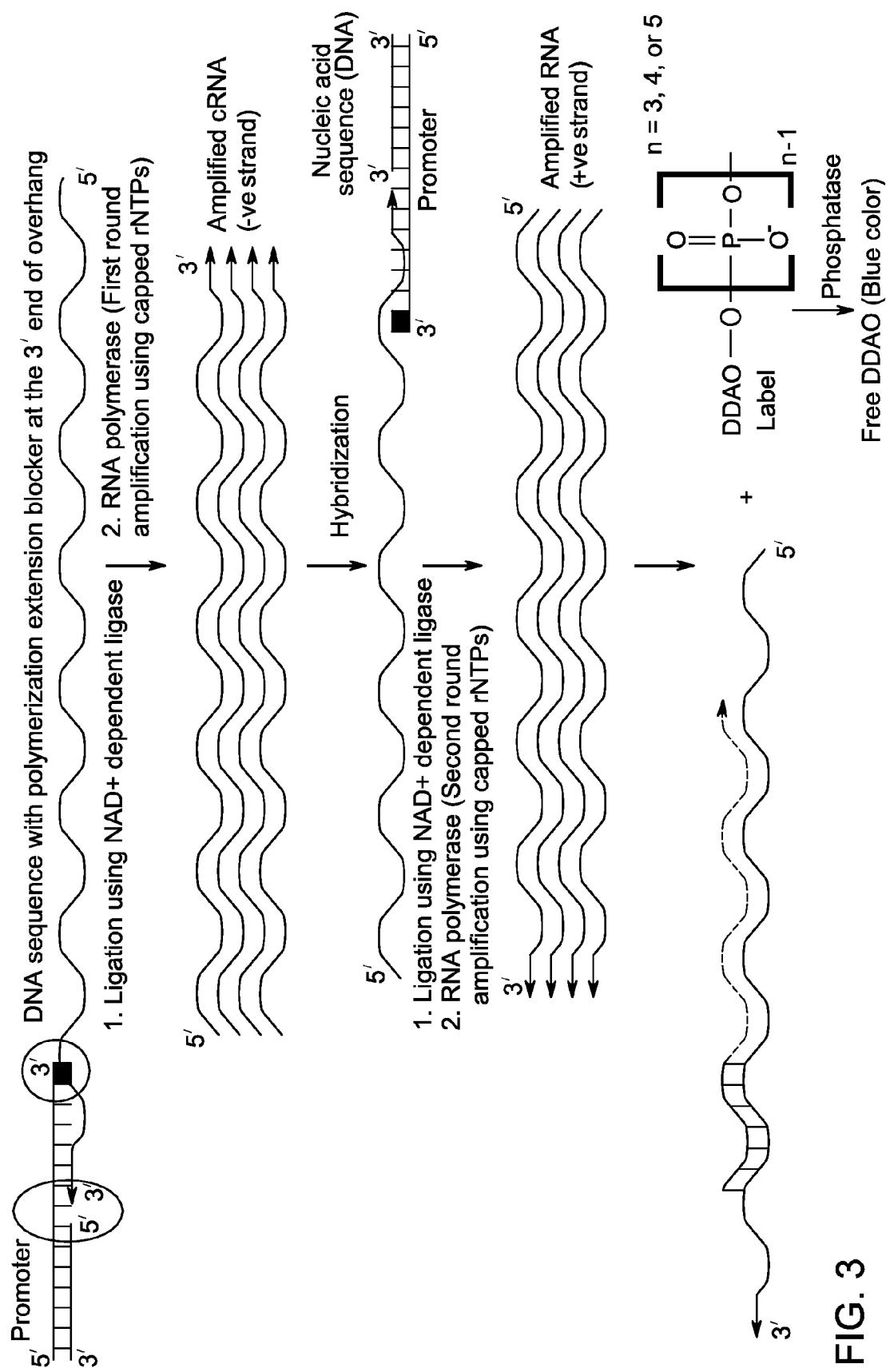
FIG. 3 is a schematic representation of simultaneous RNA amplification by initial ligation and subsequent transcription reactions followed by detection using terminal-phosphate-labeled nucleotides in a single reaction vessel.

To more clearly and concisely describe and point out the subject matter of the claimed invention, the following definitions are provided for specific terms, which are used in the following description and the appended claims.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified.

As used herein, the term "amplification" or the term "amplifying" refers to the production of multiple copies of a target nucleic acid sequence or the production multiple nucleic acid sequence copies that are complementary to the target nucleic acid sequence.

As used herein, the term "amplified RNA sequences" refers to sequences that are produced by the amplification of/amplifying the target RNA sequence using the methods provided herein. The amplified RNA sequences may be either of the same sense (the +ve strand produced in the second round and subsequent even-numbered rounds of amplification) or antisense (i.e., the –ve strand produced during the first and subsequent odd-numbered rounds of amplification) with respect to the target RNA sequences.

As used herein the terms "capping" and "capped" refers to the attachment of a suitable chemical moiety to a functional or reactive group in a molecule, which when attached masks, reduces, or prevents that functionality or reactivity. For example, the terminal phosphate group of a nucleotide may be capped with a chemical moiety so as to prevent the dephosphorylation by a phosphatase. Suitable chemical moieties that could be used for capping include, but not limited to, a detectable moiety (e.g. a dye) or an alkyl group (e.g. methyl or ethyl group).

As used herein the term "DNA-dependent RNA polymerase" refers to any RNA polymerase that recognizes a double stranded DNA promoter sequence for the initiation of its polymerase activity. Examples of RNA polymerases include, but are not limited to, T7 RNA polymerase, SP6 RNA polymerase, and T3 RNA polymerase.

As used herein the term "electrochemical tag" is an electrochemically active moiety, for example, a redox moiety. Suitable electrochemical tags include the ones having a redox potential that are easily distinguishable from the intrinsic redox potential of the nucleotides (for example, guanine may be electrochemically oxidized around 0.75 V and adenine around 1.05V). Examples of electrochemical tags include, but not limited to, 1,4-benzoquinone (–0.54 V), ferrocene (+0.307), tetracyanoquinodimethane (+0.127, –0.291), N,N, N',N'-tetramethyl-p-phenylenediamine (+0.21) and tetrathiafulvalene (+0.30).

As used herein the term "labeled polyphosphate" refers to an inorganic by-product of phosphoryl transfer that results from nucleic acid polymerase treatment of a terminal-phosphate-labeled nucleotide. The labeled polyphosphate may contain a label, which upon reaction with a phosphatase may produce a detectable species. Cleavage of the polyphosphate product of the phosphoryl transfer via phosphatase, leads to a detectable change in the label attached thereon.

As used herein the term "ligase" refers to an enzyme, which catalyzes the joining of nicks between adjacent bases of nucleic acids. For example, ligase might be any enzyme capable of forming intra- or inter-molecular covalent bonds between a 5' phosphate group and a 3' hydroxyl group. Suitable ligases may include, but not limited to T4 DNA ligase, T4 RNA ligase, and *E. coli* DNA ligase.

As used herein the term "mass tag" refers to a molecular weight moiety suitable for mass spectrometry that is readily distinguishable from other components due to difference in mass. The mass tag may range the entire spectrum and the difference in mass could be as low as a single atomic mass unit.

As used herein the term "nucleic acid polymerase" refers to an enzyme whose central function is associated with polymers of nucleic acids such as RNA and DNA. For example, a nucleic acid polymerase may catalyze the production of new DNA or RNA from an existing DNA or RNA template.

As used herein the term "nucleic acid polymerase reaction" generally refers to a reaction involving the use of nucleic acid polymerases (e.g., DNA polymerase or RNA polymerase) to synthesize nucleic acids (e.g., DNA or RNA). RNA and DNA polymerases synthesize oligonucleotides via transfer of a nucleoside monophosphate from a nucleoside triphosphate (NTP), deoxynucleoside triphosphate (dNTP) or dideoxynucleoside triphosphate (ddNTP) to the 3' hydroxyl of a growing oligonucleotide chain. The force, which drives this reaction, is the cleavage of an anhydride bond and the concomitant formation of an inorganic pyrophosphate. The synthesis or nucleic acids involves direct changes only at the α- and β-phosphoryl groups of the nucleotide, allowing nucleotides having three or more phosphate groups in polyphosphate chain with modifications at the terminal phosphate position as substrates for nucleic acid polymerase reactions.

As used herein the term "nucleoside" refers to a compound having a purine, deazapurine, pyrimidine or modified base linked to a sugar or a sugar substitute, such as a carbocyclic or acyclic moiety, at the 1' position or equivalent position and includes 2'-deoxy and 2'-hydroxyl, and 2', 3'-dideoxy forms as well as other substitutions.

As used herein the term "nucleotide" refers to both natural and modified nucleoside phosphates. The esterification site may correspond to the hydroxyl group attached to the C-5 position of the pentose sugar of the nucleoside. The nucleotides may be structurally modified so as to make them substantially non-reactive to phosphatases. Structural modifications may include capping the nucleotides with a chemical group that prevents the phosphatase from dephosphorylating the nucleotides. The capping may be achieved by attaching an alkyl group (e.g., a methyl group or an ethyl group) to the terminal phosphate of the nucleotide.

The term "oligonucleotide" as used herein includes but not limited to linear oligomers of nucleotides or derivatives thereof, including deoxyribonucleosides, ribonucleosides, and the like. Throughout the specification, whenever an oligonucleotide is represented by a sequence of letters, the nucleotides are in the 5'→3' order from left to right where A denotes adenosine, C denotes cytosine, G denotes guanosine, and T denotes thymidine.

As used herein the term "phosphatase" refers to any enzyme that cleaves phosphate monoesters, phosphate thioesters, phosphoramidate, polyphosphates, and nucleotides to release inorganic phosphate. In the context of the present invention, this enzyme does not cleave a terminally labeled nucleoside phosphate (i.e., the terminal-phosphate-labeled nucleotide is substantially non-reactive to phosphatase). The phosphatase definition herein provided specifically includes, but is not limited to, alkaline phosphatase and acid phosphatase (e.g., bacterial alkaline phosphatase, calf intestine phosphatase, artic shrimp alkaline phosphotase).

As used herein the term "polymerase extension blocker" refers to a chemical moiety which when attached to the 3' terminal end of an oligonucleotide prevents further extension of the growing nucleic acid chain from 3' end by nucleic acid polymerization reaction. Polymerase extension blocker could be a modified nucleotide (e.g. dideoxyribonucleotide). The modified nucleotide at the 3' terminal end of an oligonucleotide may be capable of blocking the extension reaction of a reverse transcriptase from the 3' terminal end.

A used herein the term "primase" refers to a RNA polymerase that is involved in DNA replication. During replication, the primase synthesizes initial RNA primers and initiates the DNA synthesis by a DNA polymerase. In bacteria, the primase binds to a DNA helicase, forming a complex, primosome. Primase is then activated by the DNA helicase and synthesizes a short RNA primer of about 11 nucleotides long, to which new nucleotides may be added by DNA polymerase.

As used herein the term "primer" refers to a linear oligonucleotide that anneals specifically to a predetermined nucleic acid sequence. The primers are designed to have a sequence, which is the reverse complement of a region of the target nucleic acid to which it anneals. Both the upper and lower limits of the length of the primer are empirically determined. The lower limit on primer length is stable hybridization since very short primers (less than 12 nucleotides long) do not form thermodynamically stable duplexes under hybridization conditions. Upper limit is determined by the possibility of a duplex formation in a region other than the predetermined interrogation target. Suitable primer lengths are in the range of about 12-100 nucleotides, preferably about 15-30 nucleotides and most preferably about 17-25 nucleotides long.

As used herein the term "target nucleic acid sequence" refers to a nucleic acid sequence whose sequence identity, or ordering or location of nucleosides is determined by one or more of the methods of the present invention. Target nucleic acid sequence may be a ribonucleic acid (RNA) of natural or synthetic origin. A target RNA sequence may be, but not limited to, messenger RNA (mRNA), transfer RNA (tRNA), ribosomal RNA, mitochondrial RNA, small nuclear RNA (snRNA), small interfering RNA (siRNA), or heterogeneous nuclear RNA (hnRNA).

As used herein the term "terminal-phosphate-labeled nucleotide" refers to nucleotide that include a structural modification at the terminal phosphate of the nucleotide. The structural modification may be the attachment of a label (e.g., chemiluminescent, fluorescent, electrochemical or chromophoric moieties, Raman-active tags or mass tags) and such modifications do not abolish the ability of the nucleotides to function in a polymerase reaction. The labels employed may be, but not limited to, an enzyme-activable label. The terminal-phosphate-labeled nucleotides may include three or more phosphate groups in the polyphosphate chain and when these terminal-phosphate-labeled nucleotides are used in nucleic acid polymerase reactions, the reaction results in production of a labeled polyphosphate.

As used herein the terms "transcription" and "transcribing" refers to the process through which a DNA or an RNA sequence is enzymatically copied by an RNA polymerase to produce a complementary RNA. Transcription proceeds in the 5'→3' direction (i.e., the template is read in the 3'→5' direction and the new, complementary fragments are generated in the 5'→3' direction). DNA-dependent RNA polymerase may be used to transcribe an RNA template if the RNA template is ligated to a double stranded DNA promoter sequence for the initiation of its polymeric activity. After transcription initiation by the RNA polymerase on the double stranded DNA region, transcription proceeds across the RNA-DNA junction and through the RNA region with no observable loss of speed or processivity. The template RNA being transcribed may be single stranded RNA, double stranded RNA or a DNA:RNA heteroduplex.

Embodiments

In some embodiments, the present invention provides methods for amplifying and detecting a target RNA sequence. The methods include the steps of amplifying the target RNA sequence to produce amplified RNA sequences, reacting the amplified RNA sequence with a nucleic acid polymerase in presence of at least one terminal-phosphate-labeled nucleotide to produce a labeled polyphosphate and detecting the labeled polyphosphate.

Samples suspected or known to contain the intended target nucleic acid may be obtained from a variety of sources. The sample may be, but not limited to a biological sample, a food or agricultural sample or an environmental sample. Sample may also be derived from a biological subject. The biological subject may be of prokaryotic or eukaryotic origin and includes viruses. Such samples may be, but not limited to the ones from/derived from biological tissue or body fluid or exudate (e.g., blood, plasma, serum or urine, milk, cerebrospinal fluid, pleural fluid, lymph, tears, sputum, saliva, stool, lung aspirates, throat or genital swabs, and the like), whole cells, cell fractions or cultures. In certain circumstances, it might be necessary or desirable to treat the sample to release and/or extract the target nucleic acid sequence for hybridization. When the target nucleic acid is present in double stranded form, it might also be necessary or desirable to denature and render hybridizable single stranded form. Target nucleic acid in the sample my be dispersed in solution or may be immobilized on a solid support (such as blots, arrays or micro titer or well plates).

Detection of target RNA sequence may be used, for example, for detection of pathogenic organisms, forensic purposes, medical diagnostic purposes, or for clinical purposes. The invention includes embodiments that relate generally to methods applicable in analytical, diagnostic, or prognostic applications.

In some embodiments, the target RNA sequence may be a heteropolymeric or a homopolymeric sequence. The target RNA sequence for detection may include a natural or synthetic RNA and/or a natural or synthetic oligoribonucleotide. It may be, but not limited to ribonucleic acid (RNA), messenger RNA (mRNA), transfer RNA (tRNA) ribosomal RNA, mitochondrial RNA, small nuclear RNA (snRNA) or small interfering RNA (siRNA) and heterogeneous nuclear RNA (hnRNA). In some embodiments, the amplification does not include the step of synthesizing an intermediate c-DNA.

In some embodiments, the amplified RNA sequences are of the same sense (amplified sense RNA sequences) as compared to the target RNA sequences. In alternative embodiments the amplified RNA sequences are of the opposite sense (amplified antisense, complementary RNA sequences) with respect to the target RNA sequences.

In some embodiments the reaction of the amplified nucleic acid sequences with a nucleic acid polymerase is a nucleic acid polymerization reaction. In some embodiments, the steps of amplifying the target RNA sequence, conducting nucleic acid polymerase reaction and detecting the labeled polyphosphate are performed in a single reaction vessel. In some embodiments, the aforementioned steps are performed in a homogeneous assay format. In some embodiments, the aforementioned steps are performed sequentially. In some embodiments, two or more of the aforementioned steps are performed simultaneously. In some embodiments, all the aforementioned steps are performed concurrently using a single, homogenous reaction mixture. In some embodiments, all the aforementioned steps are performed sequentially using a single, homogenous reaction mixture.

The presence, absence, and/or concentration of the labeled polyphosphate may be correlated to the presence, absence, and/or quantification of the target ribonucleic acid. Thus, in certain embodiments, the methods may further include the step of adding one or more additional detection reagents (e.g., labeled probe or a labeled antibody) to the polymerase reaction.

In some embodiments, the detection of the labeled polyphosphate is performed by the detection of the presence, absence, and/or concentration of labeled polyphosphate. In certain embodiments, the labeled polyphosphate is further reacted with a phosphatase to produce a detectable species. The detection of the labeled polyphosphate may be performed by reacting the labeled polyphosphate with a phosphatase to produce the detectable species and detecting the formed detectable species. A detectable species may be detectable by colorimetry, fluorescence, chemiluminescene, mass change, Raman signal, electrochemical signal, or a combination thereof.

In some embodiments, the nucleic acid polymerase reaction is conducted in presence of at least one of DNA or RNA polymerase. Suitable polymerases include, but not limited to, DNA-dependent RNA polymerases, primases, telomerases, terminal deoxynucleotidyl transferases or RNA-dependant DNA polymerases (reverse transcriptase). The nucleic acid polymerase may be a DNA polymerase, such as DNA polymerase I, II, or III; DNA polymerase α, β, γ; terminal deoxynucleotidyl transferase; or telomerase. Alternatively, the nucleic acid polymerase employed is a RNA dependent DNA polymerase (reverse transcriptase). Suitable reverse transcriptases include, but not limited to, HIV RT, MMLV RT, or DNA polymerases having reverse transcriptase activity.

In some embodiments, the nucleic acid polymerase reaction includes at least one terminal-phosphate-labeled nucleotide comprising three or more phosphate groups in the polyphosphate chain producing a labeled polyphosphate as by-product. In some embodiments, the nucleic acid polymerase reaction step may further include a phosphatase, which converts the labeled polyphosphate by-product to a detectable species. In some embodiments the nucleic acid polymerization reaction comprises incubation of the amplified RNA sequences with a primer, nucleotides, a reverse transcriptase, and at least one terminal-phosphate-labeled nucleotide. In some embodiments, the nucleic acid polymerase reaction includes at least one nucleotide, which is substantially non-reactive to phosphatase in addition to at least one terminal-phosphate-labeled nucleotide.

Nucleotides useful as substrates in the nucleic acid polymerase reaction may include, but not limited to, nucleoside polyphosphates such as deoxyribonucleoside polyphosphates, ribonucleoside polyphosphates, dideoxy nucleoside polyphosphates, carbocyclic nucleoside polyphosphates and acyclic nucleoside polyphosphates, and analogues thereof. In some embodiments the nucleotides may be capped with a blocking group that prevents the phosphatase from dephosphorylating the nucleotides. In some embodiments the capping is achieved by attaching an alkyl group to the terminal phosphate of the nucleotide. In some embodiments the alkyl groups used for capping are methyl or ethyl group.

By terminal-phosphate-labeled nucleotide, it is meant that the labeled polyphosphate concomitantly released following incorporation of the nucleoside monophosphate into the growing nucleotide chain is a detectable species or is capable of producing a detectable species.

In some embodiments, the label attached at the terminal-phosphate position in a terminal-phosphate-labeled nucleotide may include, but not limited to, chemiluminescent label, fluorescent label, fluorogenic label, chromogenic label, mass tag, Raman tag, electrochemical tag or a combination thereof. In some embodiments, the label may be detectable by the presence, absence or change of color, fluorescence emission, chemiluminescene, mass change, Raman spectrum, electrochemical signal, or a combination thereof.

In some embodiments the terminal-phosphate-labeled nucleotides comprise three or more phosphates in the polyphosphate chain. Suitable examples include nucleoside polyphosphate, such as a deoxynucleoside polyphosphate, dideoxynucleoside polyphosphate, carbocyclic nucleoside polyphosphate, or acrylic nucleoside polyphosphate and their analogues with an electrochemical, colorimetric, chemiluminescent, or fluorescent label, mass tag or a Raman tag attached to the terminal-phosphate. In some embodiments, the labeled polyphosphate is further reacted with a phosphatase to produce a detectable species. In such embodiments, the detectable species in the labeled polyphosphate is suitably masked in such a way that it is undetectable unless treated with a phosphatase. However, upon the incorporation of nucleotide monophosphate into the growing oligonucleotide chain and subsequent phosphatase treatment of the reaction, the detectable species is unmasked and becomes detectable. For example, if the hydroxyl group on the side of the triple ring structure of 1,3-dichloro-9,9-dimethyl-acridine-2-one (DDAO) is attached to the terminal-phosphate position of the nucleotide, the DDAO does not fluoresce at 659 nm.

During nucleic acid polymerase reaction, once the nucleoside monophosphate is incorporated into growing nucleic acid, the by-product, DDAO polyphosphate (which also does not fluoresce at 659 nm) is a substrate for phosphatase. Once de-phosphorylated to form DDAO, the dye moiety will become fluorescent at 659 nm and hence detectable. When dephosphorylated, DDAP-phosphate exhibits a large shift in fluorescence emission and a large increase in fluorescence intensity (DDAO-phosphate is weakly fluorescent at about 570 nm. When dephosphorylated, the fluorescence emission shifts to about 659 nm and fluorescence intensity is increased to about 20 times.) In some embodiments, the specific analysis of the polyphosphate product may be carried out in the polymerase reaction solution, eliminating the need to separate reaction products from starting materials. This allows for the detection and, optionally, quantitation of nucleic acids formed during polymerase reactions using routine instrumentation such as spectrophotometers.

In some embodiments the labeled polyphosphate by-product of phosphoryl transfer may be detected without the use of phosphatase treatment. For example, natural or modified nucleoside bases, particularly guanine, may cause quenching of fluorescence. Therefore, in a terminal-phosphate-labeled nucleotide, where the label is a fluorophore, the label may be partially quenched by the base. Upon incorporation of the nucleoside monophosphate, the label polyphosphate by-product may be detected due to its enhanced fluorescence. Alternatively, it may be possible to physically separate the labeled polyphosphate product, for example by chromatographic separation methods, before detection.

In some embodiments, the terminal-phosphate labeled nucleotide may be represented by the formula:

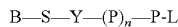

B—S—Y—(P)$_n$—P-L wherein P=phosphate (PO$_3$) and derivatives thereof, n is 2 or greater; Y is an oxygen or sulfur atom; B is a nitrogen-containing heterocyclic base; S is an acyclic moiety, carbocyclic moiety or sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P-L is a phosphorylated label which preferably becomes independently detectable when the phosphate is removed.

The sugar moiety in the terminal-phosphate-labeled nucleotide may include, but is not limited to ribosyl, 2'-deoxyribosyl, 3'-deoxyribosyl, 2',3'-dideoxyribosyl, 2',3'-didehydrodideoxyribosyl, 2'- or 3'-alkoxyribosyl, 2'- or 3'-aminoribosyl, 2'- or 3'-fluororibosyl, 2'- or 3'-mercaptoribosyl, 2'- or 3'-alkylthioribosyl, acyclic, carbocyclic and other modified sugars.

The base in the terminal-phosphate-labeled nucleotide may include, but is not limited to uracil, thymine, cytosine, 5-methylcytosine, guanine, 7-deazaguanine, hypoxanthine, 7-deazahypoxanthine, adenine, 7-deazaadenine, 2,6-diaminopurine, and analogs thereof.

Using the methods provided herein, target RNA may be amplified by a ligation-based RNA amplification method that omits an intermediate c-DNA synthesis step. In some embodiments, target RNA amplification is performed by first hybridizing the target RNA with a nucleic acid sequence that comprises a double stranded region including a promoter sequence for RNA polymerase, and a single stranded 3' terminal region capable of hybridizing to the target RNA sequence. Following hybridization, 5' end of the double stranded region of the nucleic acid sequence is ligated to the 3' end of the target RNA sequence to form a ligated sequence. The ligated sequence may then be transcribed with a RNA polymerase to form an amplified antisense, complementary RNA sequences. In some embodiments, a second round of amplification is performed on the amplified antisense complementary RNA sequences to provide amplified sense RNA sequences.

In some embodiments, the step of amplifying the target RNA sequence to produce amplified RNA sequences, comprises the steps of (i) providing the target RNA sequence other than polyA; (ii) providing one or more nucleic acid sequences comprising a double stranded region comprising a promoter sequence for RNA polymerase, and a single stranded 3' terminal region capable of hybridizing to the target RNA sequence; (iii) hybridizing the single stranded 3' terminal region of the nucleic acid sequence to the target RNA sequence; (iv) ligating 5' end of the double stranded region of the nucleic acid sequence to the 3' end of the target RNA sequence to form a ligated sequence; (v) transcribing the ligated sequence with RNA polymerase to form an amplified antisense, complementary RNA sequences. In some embodiments, amplifying the target RNA sequence further comprises performing the aforementioned steps (i)-(iv) using the amplified antisense complementary RNA as the target RNA sequence to produce amplified sense RNA sequences.

In some embodiments, two or more of the aforementioned steps are performed in single reaction vessel. Alternatively, all the aforementioned steps may be carried out in a single reaction vessel. In some embodiments the individual steps are performed step-wise. In some embodiments the RNA polymerase used is a DNA-dependent RNA polymerase. In some embodiments the DNA-dependent RNA polymerase is a T7 RNA polymerase.

The deoxyribonucleotides used in transcription reaction may be structurally modified such that they are substantially non-reactive to phosphatases, which may be achieved by capping the nucleotides with some blocking group that prevents the phosphatase from dephosphorylating the nucleotides. In some embodiments, the capping may be achieved by attaching an alkyl group (e.g., a methyl or an ethyl group) to the terminal phosphate of the nucleotide.

In some embodiments, the nucleic acid sequences comprising a double stranded region comprising a promoter sequence for RNA polymerase, and a single stranded 3' terminal region capable of hybridizing to the target RNA sequence is a synthetic nucleic acid sequence. In some of the embodiments, the nucleic acid sequence is a deoxyribonucleic acid (DNA) or oligodeoxyribonucleotide. In some embodiments the double stranded region of the nucleic acid sequences is at least about 14 nucleotide pairs long. In some embodiments the single stranded 3' terminal region capable of hybridizing to the target RNA sequence is at least 3 nucleotides long. In some embodiments, the double stranded DNA oligonucleotide comprises a promoter for RNA polymerase within the double stranded region that is followed by a segment of single stranded DNA sequence forming a 3' overhang.

The DNA oligonucleotide may further comprise a transcription initiation site. In some embodiments, the double stranded DNA oligonucleotide comprising a 3' overhang comprises a string of thymidine residues. In some embodiments, the single stranded 3' overhang region comprising a string of thymidine residues hybridizes to the 3' end of target messenger RNA (mRNA) poly (A) tails. In some embodiments, the single stranded 3' terminal region of the nucleic acid sequences capable of hybridizing to the target RNA sequence contains a modified nucleotide at the 3' terminal end. In some embodiments, the modified nucleotide is capable of blocking the extension reaction of a reverse transcriptase from the 3' terminal end. In some embodiments, the modified nucleotide is a dideoxyribonucleotide.

The promoter sequence in the nucleic acid sequences may comprise sequences that are recognized by a bacterial RNA polymerase (e.g., E. coli RNA polymerase). In some embodiments, the promoter sequence in the nucleic acid sequences comprises sequences that are recognized by a RNA polymerase from bacteriophage. Examples of RNA polymerases from bacteriophage may include, but are not limited to, T7

RNA polymerase, T3 RNA polymerase, and SP6 RNA polymerase. In some embodiments, the promoter sequence in the nucleic acid sequences comprises a promoter for bacteriophage T7 RNA polymerase.

In some embodiments, ligation of the 5' end of the double stranded region of the nucleic acid sequence to the 3' end of the target RNA sequence to form a ligated sequence is carried out by enzymatic means. In some embodiments, the ligation is performed using a DNA ligase. Suitable DNA ligases may include, but not limited to, ligases from bacteria or bacteriophages. In some embodiments the ligation is performed using a T4 DNA ligase. In some embodiments, the ligation is performed by using a DNA ligase that utilizes a cofactor that is substantially resistant to phosphatase. Suitable examples for such ligases include, but not limited to NAD+ dependent DNA ligases (ligA). Suitable NAD+ dependent DNA ligases may include, but not limited to ligases from *E. coli* or *Mycobacterium*. In some the embodiments the DNA ligase used is an *E. coli* ligase.

In some embodiments, the methods of the invention are performed under isothermal conditions wherein the temperature conditions are held substantially constant during each cycle of amplification. Suitable temperature for the reaction ranges from 15 to 50 degrees. In some embodiments, the methods of the invention are performed under isothermal conditions wherein the selected temperature is between 25 to 40 degrees.

In some embodiments, the present invention provides methods for exponential amplification and detection of a target ribonucleic acid sequence in a sample in a single reaction vessel. The method include the steps of: a) amplifying the target RNA sequence to produce amplified RNA sequences, (b) conducting a nucleic acid polymerase reaction on the amplified RNA sequences in presence of a primer and at least one terminal-phosphate-labeled nucleotide comprising three or more phosphate groups in the polyphosphate chain, resulting in the production of a labeled polyphosphate; (c) permitting the labeled polyphosphate to react with a phosphatase to produce a detectable species; and d) detecting the detectable species. In some embodiments, the aforementioned steps are performed simultaneously.

The amplification of RNA involves a promoter-based amplification without involving c-DNA intermediates. Amplification comprises the steps of (i.) providing the target RNA sequence other than polyA, (ii.) providing one or more nucleic acid sequences comprising a double stranded region comprising a promoter sequence for RNA polymerase, and a single stranded 3' terminal region capable of hybridizing to the target RNA sequence; (iii.) hybridizing the single stranded 3' terminal region of the nucleic acid sequence to the target RNA sequence; (iv.) ligating 5' end of the double stranded region of the nucleic acid sequence to the 3' end of the target RNA sequence to form a ligated sequence; (v.) transcribing the ligated sequence with RNA polymerase to form an amplified antisense, complementary RNA sequences. In some embodiments, the steps (i)-(iv) are repeated using the amplified antisense complementary RNA as the target RNA sequence to form amplified sense RNA sequences. In some embodiments, the single stranded 3' terminal region of the nucleic acid sequences capable of hybridizing to the target RNA sequence comprises a modified nucleotide at the 3' terminal end. The modified nucleotide substantially prevents the extension reaction by a reverse transcriptase from the 3' terminal end using target RNA sequence as a template. In some embodiments, the modified nucleotide is a dideoxyribonulcleotide.

In some embodiments the ligation reaction of the 5' end of the double stranded region of the nucleic acid sequence to the 3' end of the target RNA sequence comprises an ATP-independent DNA ligase. Suitable ATP-independent DNA ligases may be, but not limited to nicotinamide adenine nucleotide (NAD+)-dependent DNA ligases (lig A) such as *E. coli* ligase or mycobacterium ligase. In some embodiments, the transcription of ligated sequences is performed using modified ribonucleotides (rNTPs) that are substantially non reactive to the phosphatase. In one embodiment, the modification includes terminal phosphate modifications such as alkylating the terminal phosphate group. Suitable alkylating groups include, but are not limited to, a methyl group or an ethyl group.

In some embodiments, the nucleic acid polymerase reaction comprises incubation of amplified RNA sequences with a reverse transcriptase and modified deoxyribonucleotides (dNTPs) that are substantially resistant to phosphatase. In one embodiment, the modification of deoxyribonucleotides includes terminal phosphate modifications such as alkylation of the terminal phosphate group.

Also provided herein are kits containing the reagents required to practice the inventive methods that permit simultaneous exponential amplification and detection of target RNA sequence in a sample in a single reaction vessel. In some embodiments, the kit comprises: (a) at least one nucleic acid sequence comprising a double stranded region comprising a promoter sequence for RNA polymerase, and a single stranded 3' terminal region capable of hybridizing to the target ribonucleic acid sequence, wherein recessed 5' end is phosphorylated and the terminal 3' end is capped with a polymerase extension blocker; (b) a ligation enzyme capable of ligating the target ribonucleic acid sequence to the nucleic acid sequence in presence of a cofactor that is substantially resistant to a phosphatase; (c) nucleotides that are substantially resistant to the phosphatase; (d) at least one of DNA polymerase, RNA polymerase, an exonuclease, reverse transcriptase or combinations thereof; and (e) at least one or more terminal-phosphate-labeled nucleotide according to formula:

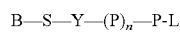

wherein P=phosphate ($PO_3$) and derivatives thereof, n is 2 or greater; Y is an oxygen or sulfur atom; B is a nitrogen-containing heterocyclic base; S is an acyclic moiety, carbocyclic moiety or sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P-L is a phosphorylated label which preferably becomes independently detectable when the phosphate is removed; and (f) the phosphatase.

In some embodiments, the nucleic acid sequence in the kit comprising a double stranded region comprising a promoter sequence for RNA polymerase, and a single stranded 3' terminal region capable of hybridizing to the target RNA sequence is a synthetic nucleic acid sequence. In some embodiments, the kit comprises a DNA oligonucleotide as the nucleic acid sequence. In some embodiments the double stranded region of the nucleic acid sequences is at least about 14 nucleotide pairs long and the single stranded 3' terminal region capable of hybridizing to the target RNA sequence is at least 3 nucleotides long. In some embodiments, the kit comprises a nucleic acid sequence comprising a promoter sequence for a DNA-dependent RNA polymerase. Suitable examples of DNA-dependent RNA polymerase may be, but not limited to T7 RNA polymerase, T4 RNA polymerase and SP6 RNA polymerase.

In some embodiments, the kit comprises a dideoxyribonucleotide as a polymerase extension blocker. In some embodiments the kit comprises a ligation enzyme having nicotinamide adenine dinucleotide (NAD+) as its cofactor. Suitable examples for NAD+ dependent ligation enzymes may include, but not limited to ligA, *E. coli* ligase, and mycobacterium ligase. In some embodiments, the kit comprises capped nucleotides wherein the capping prevents the phosphatase from dephosphorylating the nucleotides. In some embodiments, the capping is achieved by attaching an alkyl group to the terminal phosphate of the nucleotide. In some embodiments the alkyl groups used for capping are methyl or ethyl group.

In some embodiments, the kit comprises a terminal-phosphate-labeled deoxyribonucleotide. The terminal-phosphate-labeled nucleotides may comprise three or more phosphates in the polyphosphate chain. Suitable examples include, but not limited to, a nucleoside polyphosphate, such as a deoxynucleoside polyphosphate, dideoxynucleoside polyphosphate, carbocyclic nucleoside polyphosphate, or acrylic nucleoside polyphosphate and their analogues with an electrochemical label, a mass tag, a colorimetric dye or a chemiluminescent, or fluorescent label attached to the terminal-phosphate.

EXAMPLES

While only certain features of the invention have been illustrated and described herein, many modifications and changes will occur to those skilled in the art. It is, therefore, to be understood that the appended claims are intended to cover all such modifications and changes as fall within the true spirit of the invention. The present examples are provided for illustrative purposes only, and should not be construed as limiting the scope of the present invention as defined by the appended claims. All references given below and elsewhere in the specification are hereby included herein by reference.

Materials

Water: All water used in these examples, including water used to prepare electrophoresis buffer, had been treated with diethyl pyrocarbonate (DEPC) and autoclaved to remove any contaminating RNA nucleases. The water used in preparation of ligation or transcription reactions was DEPC-treated and obtained from Ambion.

PT7IVS5 (Qiagen Operon)

```
Oligo SEQ ID NO:1
5'-d[GTAATACGACTCACTATAGGGAG(T)24]-3'.
```

The deoxyriboligonucleotide (oligo) is composed of three parts.
1. The promoter sequence for T7 RNA polymerase is indicated in bold (Lopez, et al. 1997)
2. A five base intervening sequence (IVS), or that sequence complementary to the start site of transcription to where the poly(dT) sequence starts, is indicated in italics.
3. A 24 base poly(dT) sequence ($T_{24}$), or the sequence used to "capture" the mRNA 3' poly(rA) tail, is underlined.

cPT7IVS5 (Qiagen Operon)

```
Oligo SEQ ID NO:2
5'-Phosphate-d[AAAACTCCCTATAGTGAGTCGTATTAC]-3'
```

The oligo is composed of four parts and is the template for RNA synthesis.
1. The 5' phosphate group participates in covalent bond formation with the 3' hydroxyl group of mRNA.
2. Four dA residues in a row in italics promote hybridization of the 3' poly(rA) tail of mRNA.
3. The first base transcribed by the RNA polymerase is indicated by the underlined C. Synthesis would proceed towards the 5' end of the cPT7IVS5 oligo into the attached mRNA sequence.
4. Sequence complementary to the promoter sequence is indicated in bold PT7IVSI5 (Qiagen Operon)

```
Oligo SEQ ID NO:3
5'-d[AAATTAATACGACTCACTATAGGGAGACCACAACGG(T)24]-3'
```

The oligo is composed of three parts.
1. The promoter sequence for 17 RNA polymerase is indicated in bold.
2. A 15 base IVS, or that sequence complementary to the start site of transcription to where the poly(dT) sequence starts, is italicized.
3. A 24 base poly(dT) sequence ($T_{24}$), or the sequence used to capture" the mRNA 3' poly(rA) tail, is underlined.

cPT7IVSI5 (Qiagen Operon)

```
Oligo SEQ ID NO:4
5'-Phosphate-d[AAAACCGTTGTGGTCTCCTATAGTGAGTCGTATTA
ATTT]-3'
```

The oligo is composed of four parts and is the template for RNA synthesis.
1. The 5' phosphate group participates in covalent bond formation with the 3' hydroxyl group of mRNA.
2. Four dA residues in a row in italics promote complementary binding of the 3' poly(rA) tail of mRNA.
3. The first base transcribed by the RNA polymerase is indicated by the underlined C. Synthesis would proceed towards the 5' end of the cPT7IVS5 oligo through the IVS into the attached mRNA sequence.
4. Sequence complementary to the promoter sequence is indicated in bold.

RNA35 (Dharmacon)

```
Oligo SEQ ID NO:5
5'-r[UGUUG(U)30]-3'
```

A synthetic RNA designed to test ligation and transcription reactions. The 3'-hydroxyl of this molecule becomes joined to the 5'-phosphate group of the cPT7 oligos (IVS5 or IVS15) through the actions of a ligase enzyme.

RNA65 (Dharmacon)

```
Oligo SEQ ID NO:6
5'-r[UACAACGUCGUGACUGGGAAAAC(A)42]-3'
```

A synthetic RNA designed to test ligation and transcription reactions. The 3'-hydroxyl of this molecule becomes joined to the 5'-phosphate group of the cPT7 oligos (IVS5 or IVS15) through the actions of a ligase enzyme.

PT3w/T24 (Qiagen Operon)

```
Oligo SEQ ID NO:7
5'-d[AAATAATTAACCCTCACTAAAGGGAGACCACAACGG(T)24]-3'
```

The oligo is composed of three parts.
1. The promoter sequence for T3 RNA polymerase is indicated in bold (Ling M-L, et al. 1989)
2. A 15 base IVS, or that sequence complementary to the start site of transcription to where the poly(dT) sequence starts, is italicized.
3. A 24 base poly(dT) sequence ($T_{24}$), or the sequence used to "capture" the mRNA 3' poly(rA) tail, is underlined.

cPT3 (Qiagen Operon)

```
Oligo SEQ ID NO:8
5'-Phosphate-d[AAAACCGTTGTGGTCTCCCTTTAGTGAGGGTTAAT
TATTT]-3'
```

The oligo is composed of four parts and is the template for RNA synthesis.
1. The 5' phosphate group participates in covalent bond formation with the 3' hydroxyl group of mRNA.
2. Four dA residues in a row in italics promote complementary binding of the 3' poly(rA) tail of mRNA.
3. The first base transcribed by the RNA polymerase is indicated by the underlined C. Synthesis would proceed towards the 5' end of the cPT7IVS5 oligo through the IVS into the attached mRNA sequence.
4. Sequence complementary to the promoter sequence is indicated in bold.

```
Oligo SEQ ID NO:9
ATCCG
```

The oligo is a primer for DNA synthesis and is an artificial sequence

```
Oligo SEQ ID NO:10
TAGGCCGCTG
```

The oligo is a template for DNA synthesis and is an artificial sequence

```
Oligo SEQ ID NO:11
TAGGCTGCTG
```

The oligo is a template for DNA synthesis and is an artificial sequence

Example 1

Ligation of Double Stranded DNA to Synthetic RNA

All ligation reaction components except *E. coli* DNA Ligase (New England Biolabs; 10 units/μL) were mixed as indicated in Table 1. The reactions were heated at 60° C. for five minutes and allowed to cool to room temperature. *E. coli* DNA Ligase was added to the appropriate tubes and the reactions incubated at 30° C. for two hours. Each reaction was stopped by the addition of 1 μL RNase-free 0.5 M EDTA (US Biochemicals, Inc.).

TABLE 1

Ligation reaction formulations for Example 1.

| Component | ID 1 | ID 2 | ID 3 | ID 4 | ID 5 | ID 6 |
|---|---|---|---|---|---|---|
| Water (Ambion) | 16 μL | 15 μL | 16 μL | 15 μL | 14 μL | 13 μL |
| 10X *E. coli* ligase buffer | 2 μL | 2 μL | 2 μL | 2 μL | 2 μL | 2 μL |
| SUPERase In (Ambion 20 Units/μL) | 1 μL | 1 μL | 1 μL | 1 μL | 1 μL | 1 μL |
| PT7IVS15 (15 pmol/μL) | 1 μL | 1 μL | | | | |
| CpT7IVS15 (15 pmol/μL) | | | 1 μL | 1 μL | | |
| RNA35 (16 pmol/μL) | | | | | 3 μL | 3 μL |
| *E coli* Ligase | | 1 μL | | 1 μL | | 1 μL |
| Total Volume | 20 μL | 20 μL | 20 μL | 20 μL | 20 μL | 20 μL |

| Component | ID 7 | ID 8 | ID 9 | ID 10 | ID 11 | ID 12 |
|---|---|---|---|---|---|---|
| Water (Ambion) | 15 μL | 14 μL | 12 μL | 11 μL | 15 μL | 14 μL |
| 10X *E. coli* ligase buffer | 2 μL | 2 μL | 2 μL | 2 μL | | |
| SUPERase In (Ambion 20 Units/μL) | 1 μL | 1 μL | 1 μL | 1 μL | 1 μL | 1 μL |
| PT7IVS15 (15 pmol/μL) | 1 μL | 1 μL | 1 μL | 1 μL | 1 μL | 1 μL |
| CpT7IVS15 (15 pmol/μL) | 1 μL | 1 μL | 1 μL | 1 μL | | |
| RNA35 (16 pmol/μL) | | | 3 μL | 3 μL | 3 μL | 3 μL |
| *E coli* Ligase | | 1 μL | | 1 μL | | 1 μL |
| Total Volume | 20 μL | 20 μL | 20 μL | 20 μL | 20 μL | 20 μL |

Five-microliter samples of every reaction were mixed with 5 μL of Gel Loading Buffer II (Ambion) and heat denatured at 95° C. for two minutes. The entire amount of each sample was loaded into separate wells of 15% acrylamide, 7M urea TBE gels (Invitrogen) and subjected to electrophoresis at room temperature following the manufacturer's recommendations. Samples were loaded in numerical order from left to right, respectively, with DNA molecular weight makers interspersed. Electrophoresis was stopped when the bromophenol blue (BPB) loading dye was at the bottom of the gel. Each gel was stained by soaking in a 1:200 dilution of SYBR Gold Dye (Molecular Probes) in water for 10 minutes. After staining the gels were rinsed with distilled water and the DNA bands visualized by scanning in a Typhoon™ 8600 Variable Mode Imager (Typhoon; GE Healthcare Bio-Sciences).

The DNA molecular weight markers are a mixture of 100 Base-Pair Ladder (0.5 μg), Homo-Oligomeric $pd(A)_{40-60}$ ($1.25 \times 10^{-3}$ $A_{260}$ Units) and Oligo Sizing Markers (8-32 bases; 0.75 μL; all from GE Healthcare Bio-sciences).

The gels were scanned using the green (532) laser and fluorescein 526 SP emission filter. The results show that the three separate nucleic acid components of the ligation reaction do not form self-ligation products: The results also show a band of the appropriate size (75 bases) in the complete reaction to be the expected product of the cPT7IVSI5 and RNA35 ligation (DNA:RNA hybrid).

Example 2

Three Different Ligases Will Ligate Double Stranded DNA to RNA

All ligation reaction components other than the ligase enzymes were mixed as indicated in Table 2. The reactions were heated at 60° C. for five minutes and allowed to cool to room temperature. Different ligase enzymes were added to the appropriate tubes and the reactions incubated at 30° C. for two hours. Each reaction was stopped by the addition of 1 μL RNase-free 0.5 M EDTA (US Biochemicals, Inc.).

TABLE 2

Ligation reaction formulations for Example 2. 10x ligation buffers were supplied with the enzymes.

| Component | 1 | 2 | 3 | 4 | 5 | 6 | 7 | 8 |
|---|---|---|---|---|---|---|---|---|
| Water | 10 μL | 9 μL | 12 μL | 11 μL | 12 μL | 11 μL | 13 μL | 12 μL |
| 10X E. coli ligase buffer | 2 μL | 2 μL | | | | | | |
| 10X T4 DNA ligase buffer | | | 2 μL | 2 μL | | | | |
| 10X T4 RNA ligase buffer | | | | | 2 μL | 2 μL | 2 μL | 2 μL |
| SUPERase In (Ambion 20 Units/μL) | 1 μL | 1 μL | 1 μL | 1 μL | 1 μL | 1 μL | | 1 μL |
| 5 mM NAD | 2 μL | 2 μL | | | | | | |
| PT7IVS15 (15 pmol/μL) | 1 μL | 1 μL | 1 μL | 1 μL | 1 μL | 1 μL | | |
| CpT7IVS15 (15 pmol/μL) | 1 μL | 1 μL | 1 μL | 1 μL | 1 μL | 1 μL | 1 μL | 1 μL |
| $RNA_{35}$ (16 pmol/μL) | 3 μL | 3 μL | 3 μL | 3 μL | 3 μL | 3 μL | 3 μL | 3 μL |
| E. coli ligase (NEBL 400 Units/μL) | | 1 μL | | | | | | |
| T4 DNA ligase (NEBL 400 Units/μL) | | | | 1 μL | | | | |
| T4 RNA ligase (NEBL 10 Units/μL) | | | | | | 1 μL | | 1 μL |
| Total Volume | 20 μL | 20 μL | 20 μL | 20 μL | 20 μL | 20 μL | 20 μL | 20 μL |

Figure 4:
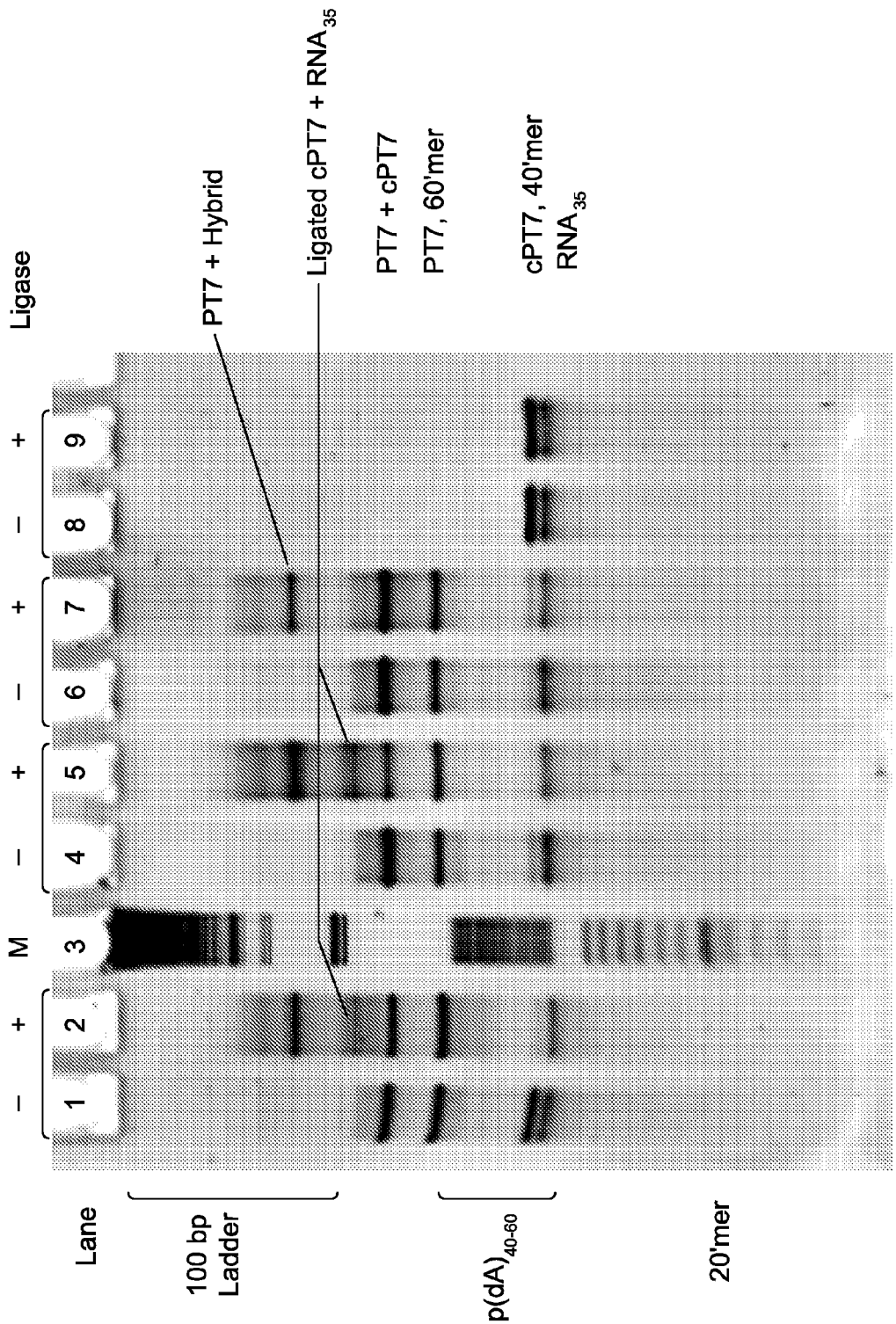
FIG. 4 is a fluoroimage of the 15% 7M urea TBE gel showing that three different ligases (*E. coli* ligase, T4 DNA ligase and T4 RNA ligase) can ligate a double stranded DNA to RNA.

Five microliter samples of every reaction were mixed with 5 μL of Gel Loading Buffer II (Ambion) and heat denatured at 95° C. for two minutes. The entire amount of each sample was loaded into separate wells of a 15% acrylamide, 7M urea TBE gel (Invitrogen) and subjected to electrophoresis at room temperature following the manufacturer's recommendations. Samples were loaded in numerical order from left to right, respectively, with DNA molecular weight makers interspersed. Electrophoresis was stopped when the BPB loading dye was at the bottom of the gel. The gel was stained by soaking in a 1:200 dilution of SYBR Gold Dye (Molecular Probes) in water for 10 minutes. After staining the gel was rinsed in distilled water and the DNA bands visualized by scanning in a Typhoon (GE Healthcare Bio-sciences). FIG. 4 is the fluoroimage of the gel. The gel was scanned using the same parameters as in Example 1.

The DNA molecular weight markers seen in lane 3 are a mixture of 100 Base-Pair Ladder (0.5 μg), Homo-Oligomeric pd(A)$_{40-60}$ (1.25×10$^{-3}$ A$_{260}$ Units) and Oligo Sizing Markers (8-32 bases; 0.75 μL; all from GE Healthcare Bio-sciences). Lanes 1 and 2 contain E. coli ligase DNA ligase (reactions 1 and 2, respectively). Lanes 4 and 5 contain T4 DNA ligase reactions (reactions 3 and 4, respectively). Lanes 6-9 contain T4 RNA ligase reactions (reactions 5, 6, 7 and 8, respectively). Ligation products are seen in lanes 2, 5, and 7, indicating that all three ligases function to ligate a DNA 5'-phosphate group to a RNA 3'-hydroxyl group. No ligation product was seen in Lane 9 (reaction 8) presumably because, lacking the PT7IVSI5 oligo, this ligation reaction will take longer to accumulate products.

Example 3

Ligated RNA May be Transcribed

All ligation reaction components except E. coli DNA Ligase were mixed as indicated in Table 3. The reactions were heated at 60° C. for five minutes and allowed to cool to room temperature. E. coli DNA Ligase was added to the appropriate tubes and the reactions incubated at 16° C. for two hours. Each reaction was stopped by the addition of 1 μL RNase-free 0.5 M EDTA (US Biochemicals, Inc.).

TABLE 3

Ligation reaction formulations for Example 3.

| Component | 1 | 2 | 3 | 4 |
|---|---|---|---|---|
| Water (Ambion) | 12 μL | 12 μL | 12 μL | 11 μL |
| 10X E. coli ligase buffer | 2 μL | 2 μL | 2 μL | 2 μL |
| SUPERase In (Ambion 20 Units/μL) | 1 μL | 1 μL | 1 μL | 1 μL |
| PT7IVS5 (15 pmol/μL) | 1 μL | 1 μL | | |
| CpT7IVS5 (5 pmol/μL) | 1 μL | 1 μL | | |
| PT7IVS15 (15 pmol/μL) | | | 1 μL | 1 μL |
| CpT7IVS15 (5 pmol/μL) | | | 1 μL | 1 μL |
| $RNA_{35}$ (5 pmol/μL) | 3 μL | 3 μL | 3 μL | 3 μL |
| E coli Ligase | | 1 μL | | 1 μL |
| Total Volume | 20 μL | 20 μL | 20 μL | 20 μL |

Five microliter samples of every reaction were mixed with 5 μL of Gel Loading Buffer II (Ambion) and heat denatured at 95° C. for two minutes. The entire amount of each sample was loaded into separate wells of a 15% acrylamide, 7M urea TBE gel (Invitrogen) and subjected to electrophoresis at room temperature following the manufacturer's recommendations. Samples were loaded in numerical order from left to right, respectively, along with an RNA molecular weight maker (Decade™ Markers from Ambion). Electrophoresis was stopped when the BPB loading dye was at the bottom of the gel. The gel was stained by soaking in a 1:200 dilution of SYBR Gold Dye (Molecular Probes) in water for 10 minutes. After staining the gel was rinsed in distilled water and the DNA bands visualized by scanning in a Typhoon (GE Healthcare Bio-Sciences).

The gel was scanned using the same parameters as in Example 1. Expected ligation products were seen from reactions 2 and 4 (Table 3), respectively.

Amplification was accomplished using aliquots of reactions 2 and 4 and MEGAscript™ T7 Kit (Ambion) as outlined in Table 4. All components were mixed together and incubated at 37° C. for one hour.

TABLE 4

Amplification reactions for Example 3.

| Component | ID 1 | 2 | 3 | 4 |
|---|---|---|---|---|
| Water (Ambion) | 2.6 μL | 0.6 μL | 2.6 μL | 0.6 μL |
| 10X Reaction Buffer | 2 μL | 2 μL | 2 μL | 2 μL |
| SUPERase In (Ambion 20 Units/μL) | 1 μL | 1 μL | 1 μL | 1 μL |
| Example 3 Reaction 2 | 4 μL | 4 μL | | |
| Example 3 Reaction 4 | | | 4 μL | 4 μL |
| 20 mM MgCl$_2$ | 4 μL | 4 μL | 4 μL | 4 μL |
| 10 mM NTP mix | 6.4 μL | 6.4 μL | 6.4 μL | 6.4 μL |
| T7 Enzyme mix | | 2 μL | | 2 μL |
| Total Volume | 20 μL | 20 μL | 20 μL | 20 μL |

Following incubation, amplification reactions 2 and 4 were each split into equal aliquots. One aliquot of each reaction had 0.5 μL 0.5 M EDTA added and were stored on ice until gel analysis. The remaining aliquots were heated at 70° C. for 5 minutes to inactivate the SUPERase In. Each heated aliquot had 1 μl of RNase A (44 Units; US Biochemical, Inc.) added and were incubated for 10 minutes at 37° C. The RNase digests were each stopped by the addition of 0.5 μL 0.5 M EDTA. Five microliter samples of every reaction were mixed with 5 μL of Gel Loading Buffer II (Ambion) and heat denatured at 95° C. for two minutes. The entire amount of each sample was loaded into separate wells of a 15% acrylamide, 7M urea TBE gel (Invitrogen) and subjected to electrophoresis at room temperature following the manufacturer's recommendations. Electrophoresis was stopped when the BPB loading dye was approximately 2 cm from the bottom of the gel. The gel was stained by soaking in a 1:200 dilution of SYBR Gold Dye (Molecular Probes) in water for 10 minutes. After staining the gel was rinsed in distilled water and the DNA bands visualized by scanning in a Typhoon (GE Healthcare Bio-Sciences). The gel was scanned using the same parameters as in Example 1.

Transcription reaction products from reactions 2 and 4, respectively were, in general, typical of a T7 RNA polymerase (RNAP) reaction. A runoff transcript of the expected 9 nucleotides (nt) was observed situated above the BPB dye. This short runoff transcript results from unligated PT7IVS5 and cPT7IVS5 oligos carried over from the ligation reaction. T7 RNAP is known to perform a non-templated addition of one nucleotide in runoff reactions (Arnaud-Barbe, et al. 1998) and this was seen just above the 9 nt product. Additionally, the RNAP, after binding to the double stranded DNA promoter, is also known to go through rounds of abortive transcription (Lopez, et al. 1997) until a long enough nascent transcript has been synthesized for the polymerase to clear the promoter. Abortive transcription products were observed below the 9 nt product in reaction 2. Surprisingly, this reaction did not contain no runoff transcript in the expected size range of 44 nt. Instead a smear of RNA was observed higher in the gel that suggests a heterodisperse population of product sizes (non-specific products). An RNA smear disappeared upon treatment with RNase A but the DNA bands remained. This smearing is another trait of T7 RNAP (Macdonald, et. al., 1993) and results from the enzyme slipping forward and backward during polymerization along homopolymeric templates.

The same types of reaction products were observed in the transcriptions containing PT7IVSI5 and cPT7IVSI5 oligos. An expected 19 nt runoff transcript from the carryover of un-ligated oligos from the ligation reaction were observed as well as smaller abortive transcripts. However, the non-templated addition of a nucleotide (nt) was obscured by what appears to be a stuttering of the polymerase as it enters the RNA portion of the DNA:RNA hybrid. Again, no expected transcript size of 75 nt was observed, but rather an RNA smear that disappeared with RNase A treatment. The RNA smear was denser in some reactions suggesting that the longer IVS allows the RNAP to enter the RNA portion of the DNA:RNA hybrid more efficiently.

Example 4

Ligation and Amplification of Double Stranded DNA to mRNA

All components were mixed as indicated in Table 5 and incubated at 30° C. for 15 minutes. There was no annealing step included in this example. Besides ligation of cPT7IVSI5 to RNA35, skeletal muscle polyA RNA (smRNA; Russian Cardiology Research and Development Center) was also used as a ligation target for this system. Each reaction was stopped by the addition of 1 μL RNase-free 0.5 M EDTA (US Biochemicals, Inc.).

TABLE 5

Ligation reaction formulations for Example 4. The 10x Ligation Buffer and T4 DNA Ligase were certified RNase-free and supplied by Takara.

| Component | ID 1 | 2 | 3 | 4 | 5 |
|---|---|---|---|---|---|
| Water (Ambion) | 3.9 μL | 6.6 μL | 2.9 μL | 3.9 μL | 2.9 μL |
| 10X Ligation Buffer | 2 μL | 2 μL | 2 μL | 2 μL | 2 μL |
| SUPERase In | 1 μL | 1 μL | 1 μL | 1 μL | 1 μL |
| PT7IVS15(15 pmol/μL) | 1 μL | | 1 μL | 1 μL | 1 μL |
| cPT7IVS15(5 pmol/μL) | 2.7 μL | | 2.7 μL | 2.7 μL | 2.7 μL |

TABLE 5-continued

Ligation reaction formulations for Example 4. The 10x
Ligation Buffer and T4 DNA Ligase were certified RNase-free and supplied by Takara.

| Component | ID | | | | |
|---|---|---|---|---|---|
| | 1 | 2 | 3 | 4 | 5 |
| SmRNA (1 µg/µL) | 1 µL | 1 µL | 1 µL | | |
| RNA35(16 pmol/µL) | | | | 1 µL | 1 µL |
| 50% PEG 8000 | 8.4 µL | 8.4 µL | 8.4 µL | 8.4 µL | 8.4 µL |
| T4 DNA Ligase(350 Units/µL) | | 1 µL | 1 µL | | 1 µL |
| Total Volume | 20 µL | 20 µL | 20 µL | | 20 µL |

Five microliter samples of every reaction were mixed with 5 µL of Gel Loading Buffer II (Ambion) and heat denatured at 95° C. for two minutes. The entire amount of each sample was loaded into separate wells of a 15% acrylamide, 7M, urea TBE gel (Invitrogen) and subjected to electrophoresis at room temperature following the manufacturer's recommendations. Electrophoresis was stopped when the BPB loading dye was approximately 2 cm from the bottom of the gel. The gel was stained by soaking in a 1:200 dilution of SYBR Gold Dye (Molecular Probes) in water for 10 minutes. After staining the gel was rinsed in distilled water and the DNA bands visualized by scanning in a Typhoon (GE Healthcare Bio-Sciences). The gel was scanned using the same parameters as in Example 1. The expected ligation product of the oligos with the RNA35 was seen in reaction 5.

Amplification was carried out using aliquots of reactions I and 3 and MEGAscript™ T7 Kit (Ambion) as outlined in Table 6. All components were mixed together and incubated at 37° C. for one hour.

TABLE 6

Reaction for example 4

| Component | |
|---|---|
| 75 mM ATP | 2.8 µL |
| 75 mM CTP | 2.8 µL |
| 75 mM GTP | 2.8 µL |
| 75 mM UTP | 2.8 µL |
| Total Volume | 11.2 µL |

Reaction setup

| Component | ID | |
|---|---|---|
| | 1 | 2 |
| NTP Mix | 11.2 µL | 11.2 µL |
| Water | 15.8 µL | 15.8 µL |
| 10x Transcription Buffer | 4 µL | 4 µL |
| SUPERase In | 1 µL | 1 µL |
| Ligation #1 | 4 µL | |
| Ligation #3 | | 4 µL |
| T7 Enzyme Mix | 4 µL | 4 µL |
| Total Volume | 40 µL | 40 µL |

Figure 5:
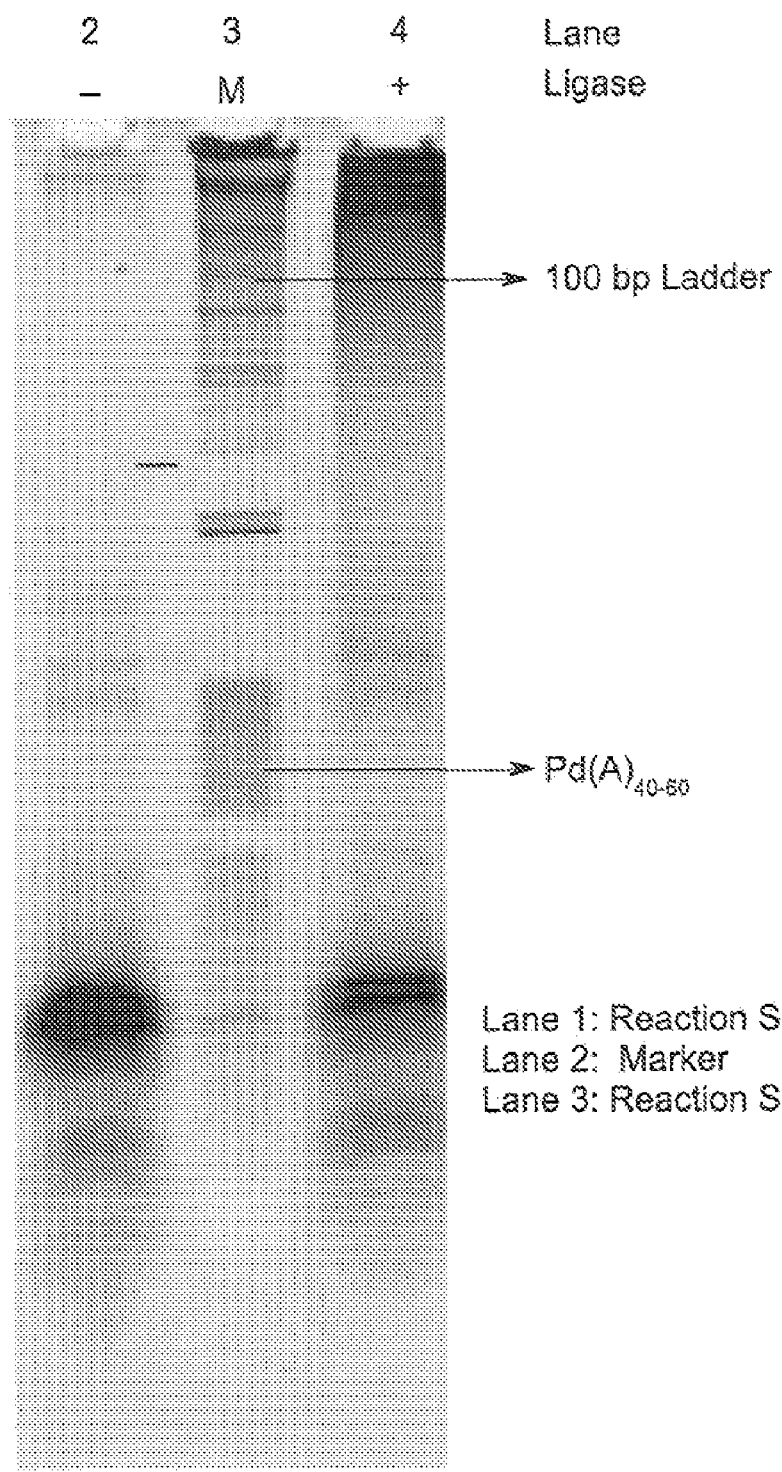
FIG. 5 is a fluoroimage of the 15% 7M Urea TBE gel showing the ligation-based amplification of mRNA.

The reactions were each stopped by the addition of 1 µL 0.5 M EDTA. Five microliter samples of every reaction were mixed with 5 µL of Gel Loading Buffer II (Ambion) and heat denatured at 95° C. for two minutes. The entire amount of each sample was loaded into separate wells of a 15% acrylamide, 7M urea TBE gel (Invitrogen) and subjected to electrophoresis at room temperature following the manufacturer's recommendations. Electrophoresis was stopped when the BPB loading dye was approximately 2 cm from the bottom of the gel. The gel was stained by soaking in a 1:200 dilution of SYBR Gold Dye (Molecular Probes) in water for 10 minutes. After staining the gel was rinsed in distilled water and the DNA bands visualized by scanning in a Typhoon (GE Healthcare Bio-Sciences). The gel was scanned using the same parameters as in Example 1. FIG. 5 is the fluoroimage of the gel.

Lane 1 and 3 in FIG. 5 show both run off and abortive transcripts as well as a single base non-templated nucleotide addition, much as was observed in Example 3. The RNA smear at the top of the gel in lane 3 (reaction 2, Table 6), along with the relative decrease in intensity of the runoff transcript when compared to lane 1 (reaction 1, Table 6) suggests the capability of this system (reaction 2, Table 6) to both anneal, ligate a double stranded DNA RNAP promoter to mRNA and transcribe complementary RNA from a DNA:mRNA hybrid.

Example 5

Nucleic Acid Sequence Detection Using Polymerase Incorporation of Gamma Phosphate-Labeled Dideoxynucleotide, ddGTP Reactions were assembled at room temperature (23° C.) using γ-(4-trifluoromethylcoumarinyl)ddGTP (ddGTP-CF3-Coumarin) Reactions contained primer template combinations having a single oligonucleotide primer (represented by SEQ ID NO: 9) annealed to one of two different oligonucleotide templates with either a dC or a dT as the next template nucleotide adjacent the 3' terminus of the primer, corresponding to SEQ ID NO: 10 and SEQ ID NO: 11, respectively.

Figure 6:
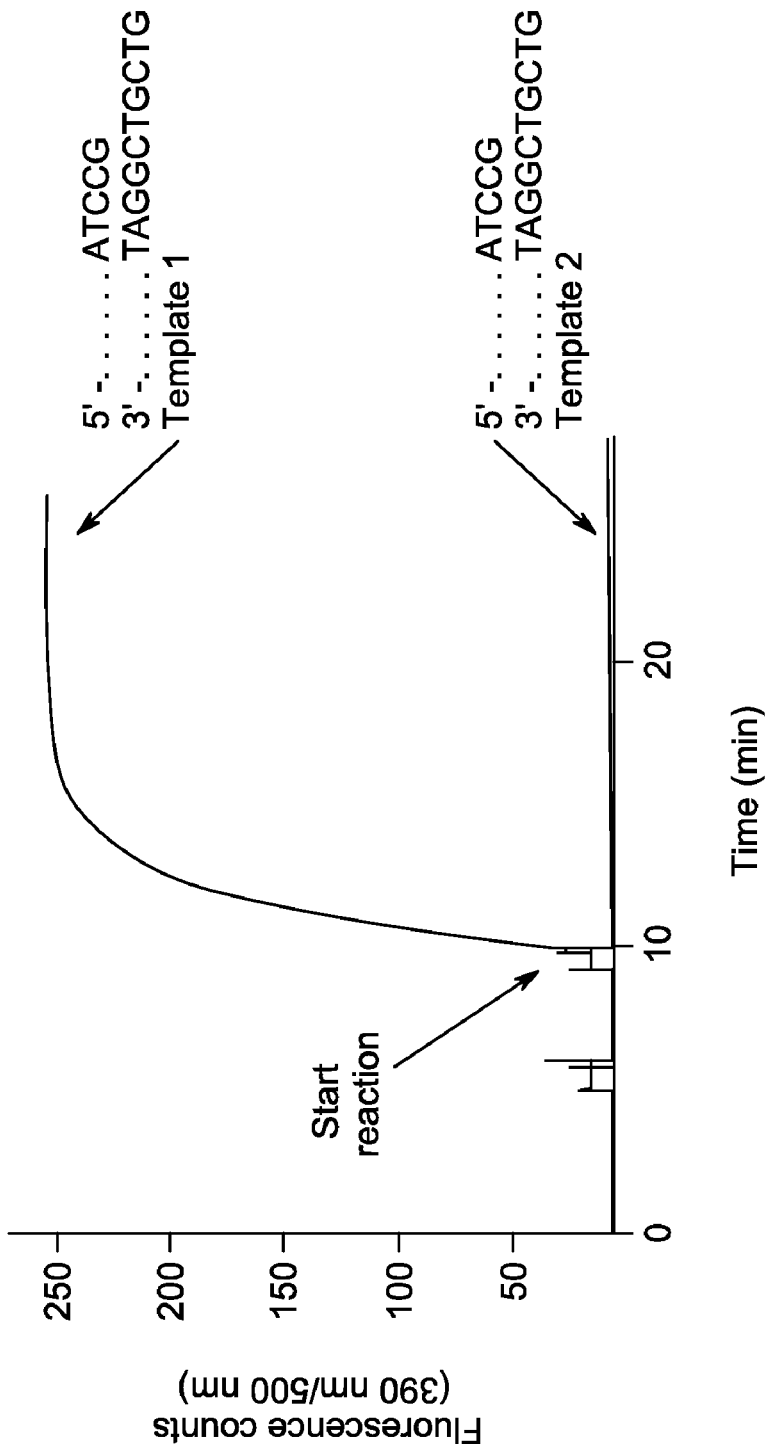
FIG. 6 is a graph showing fluorescence obtained by polymerase utilization of gamma-phosphate-labeled ddGTP in a template-directed process in the presence of phosphatase.

Referring now to FIG. 6 for template 1 (SEQ ID NO: 10) in the present example, DNA polymerase would be expected to extend the primer with labeled ddGTP. Similarly, for template 2 (SEQ ID NO: 11) in FIG. 6, DNA polymerase would be expected to extend the primer with ddATP, but not with labeled ddGTP.

Reaction conditions: A 70 µl reaction containing 25 mM Tris, pH 8.0, 5% glycerol 5 mM MgCl 2, 0.5 mM beta-mercaptoethanol, 0.01% tween-20, 0.25 units shrimp alkaline phosphatase, 100 nM primer annealed to template (the next template nucleotide is either dCMP or dTMP, as indicated), and 2 µM ddGTP-CF3-Coumarin was assembled in a quartz fluorescence ultra-microcuvet in a LS-55 Luminescence Spectrometer (Perkin Elmer), operated in time drive mode. Excitation and emission wavelengths are 390 nm and 500 nm respectively. Slit widths were 5 nm for excitation slits, 15 nm for emission slits. The reaction was initiated by the addition of 0.35 μl (11 units) of a cloned DNA polymerase I genetically engineered to eliminate 3'-5' exonuclease activity, 5'-3' exonuclease activity and discrimination against dideoxynucleotides and 0.25 mM MnCl2.

As shown in FIG. 6, for reactions containing the gamma labeled ddGTP, dye emission was detected only with Primer: Template 1, where the next nucleotide in the template was a dC. Cleavage of the pyrophosphate product of phosphoryl transfer by shrimp alkaline phosphatase leads to a detectable change in the CF3-coumarin label, which allows for the detection of the nucleic acid. No detectable dye emission was obtained with Primer: Template 2.

Example 6

Nucleic Acid Sequence Detection Using Polymerase Incorporation of Gamma Phosphate-Labeled Dideoxynucleotide, ddATP Reactions were assembled at room temperature (23° C.) using the dideoxynucleotide, γ-(3-cyanocoumarinyl)ddATP (ddATP-CN-Coumarin). Reactions contained primer: template combinations having a single oligonucleotide primer (SEQ ID NO: 9) annealed to one of two different oligonucleotide templates with either a dC or a dT as the template nucleotide, adjacent to the 3' terminus of the primer, corresponding to SEQ ID NO: 10 and SEQ ID NO: 11, respectively.

Figure 7:
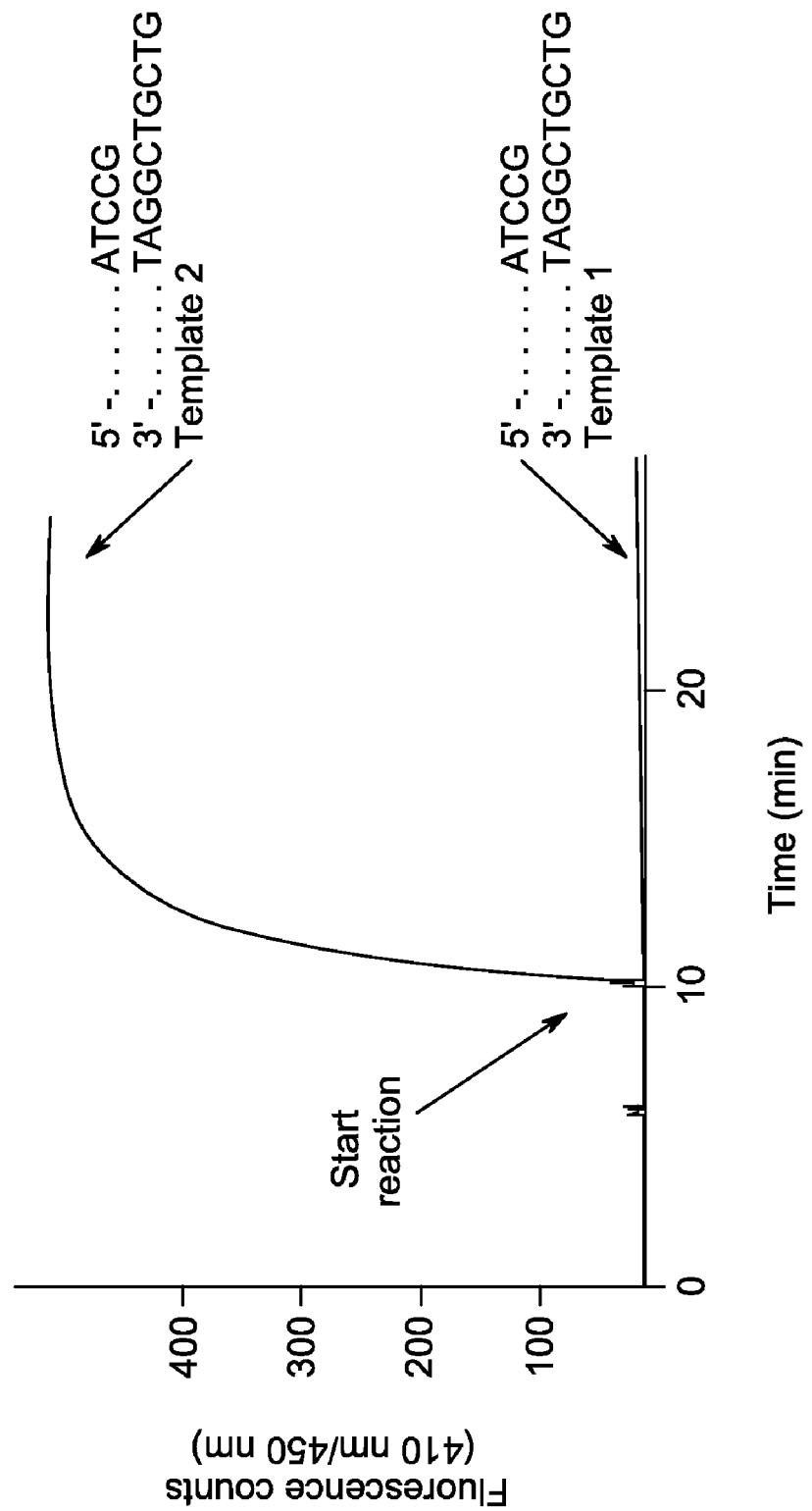
FIG. 7 is a graph showing fluorescence obtained by polymerase utilization of gamma-phosphate-labeled ddATP in a template-directed process in the presence of phosphatase.

Referring now to FIG. 7 for template 2 (SEQ ID NO: 11) in the present example, DNA polymerase would be expected to extend the primer with labeled ddATP. Similarly, for template 1 (SEQ ID NO: 10) in FIG. 7, DNA polymerase would be expected to extend the primer with ddGTP, but not with labeled ddATP.

Reaction conditions: A 70 μl reaction containing 25 mM Tris, pH 8.0, 5% glycerol 5 mM MgCl 2, 0.5 mM beta-mercaptoethanol, 0.01% tween-20, 0.25 units shrimp alkaline phosphatase, 100 nM primer annealed to template, and 2 μM ddATP-CN-Coumarin was assembled in a quartz fluorescence ultra-microcuvet in a LS-55 Luminescence Spectrometer (Perkin Elmer), operated in time drive mode. Excitation and emission wavelengths are 410 nm and 450 nm respectively. Slit widths were 5 nm for excitation slits, 15 nm for emission slits. The reaction was initiated by the addition of 0.35 μl (11 units) of a cloned DNA polymerase I genetically engineered to eliminate 3'-5' exonuclease activity, 5'-3' exonuclease activity and discrimination against dideoxynucleotides and 0.25 mM MnCl2.

As shown in FIG. 7, for reactions containing the gamma labeled ddATP, dye emission was detected only for Primer: Template 2, where the next nucleotide in the template was a dT. Cleavage of the pyrophosphate product of phosphoryl transfer by shrimp alkaline phosphatase produces a detectable change in the CN-coumarin label that permitting detection of the nucleic acid. No detectable dye emission was obtained with Primer:Template 1.

Example 7

Simultaneous RNA Amplification and Detection in a Single Reaction Vessel Using Terminal Phosphate Labeled Nucleotides Reaction Conditions: Mix together the following components and incubated at 37 degrees in a plate reader. Buffer (50 mM Tris:HCl, pH=8.0, 7 mM MgCl2, 1 mM DDT, 0.01% tween-20), 20 ng of target RNA, 30 pmoles of promoter/primer construct (with phosphorylated 5' recessed end and 3' dideoxy extension blocker), 100 micromolar NAD, 1 units *E. coli* DNA ligase, 200 micromolar capped ribonucleotides (e.g. rN4P-methyl), 20 units T7 RNA polymerase, 20 pmoles specific primer for RNA of interest, 20 units MMLV reverse transcriptase, 200 micromolar terminal-phosphate-labeled nucleotides (e.g. dN4P-DDAO) and 0.1 unit Bacterial alkaline phosphatase.

The development of signal from the phosphatase may be visualized using the naked eye or an automated device such as a plate reader with an excitation wavelength of 646 nm at an emission wavelength of 659 nm.

EQUIVALENTS

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

The invention claimed is:

1. A method for producing a labeled polyphosphate using amplified RNA sequences, comprising:
   (a) amplifying a target RNA sequence to produce the amplified RNA sequences; and
   (b) reacting the amplified RNA sequences with a nucleic acid polymerase in presence of at least one terminal-phosphate-labeled nucleotide to produce the labeled polyphosphate, wherein the labeled polyphosphate comprises three or more phosphate groups.

2. The method of claim 1, further comprising the step (c) of detecting the labeled polyphosphate.

3. The methods of claim 2, wherein the amplification step and the detection step are performed in a single reaction vessel.

4. The methods of claim 2, wherein each of the steps (a), (b), and (c) occur substantially simultaneously.

5. The method of claim 1, wherein the target RNA sequence is hetero-polymeric.

6. The method of claim 1, wherein the amplified RNA sequences are antisense cRNA to the target RNA sequence.

7. The method of claim 1, wherein the amplified RNA sequences are the same sense as the target RNA sequence.

8. The method of claim 1, wherein the reacting step comprises incubation of the amplified RNA sequences with a reverse transcriptase, nucleotides, and a primer.

9. The method of claim 8, wherein the primer is complementary to an internal sequence of the amplified RNA sequences.

10. The method of claim 8, wherein the primer consists of about 10 to about 40 nucleotides 11. The method of claim 8, wherein the nucleotides are structurally modified to be substantially non-reactive to phosphatases.

12. The method of claim 2, wherein the labeled polyphosphate is reacted with a phosphatase to produce a detectable species and detecting the formed detectable species.

13. The method of claim 12, wherein the detectable species is produced in amounts substantially proportional to the amount of the target RNA sequence.

14. The method of claim 2, further comprising the step of quantifying the target RNA sequence.

15. The method of claim 1, wherein the amplification of the target RNA sequence, comprising:
   providing the target RNA sequence other than poly A;
   providing one or more nucleic acid sequences comprising a double stranded region comprising a promoter sequence for RNA polymerase, and a single stranded 3' terminal region capable of hybridizing to the target RNA sequence;
   hybridizing the single stranded 3' terminal region of the nucleic acid sequence to the target RNA sequence;
   ligating 5' end of the double stranded region of the nucleic acid sequence to 3' end of the target RNA sequence to form a ligated sequence; and
   transcribing the ligated sequence with RNA polymerase to form amplified antisense, complementary RNA sequences.

16. The method of amplification of claim 15, further comprising:
   (a) providing the amplified antisense, complementary RNA sequence;
   (b) providing one or more nucleic acid sequences comprising a double stranded region comprising a promoter sequence for RNA polymerase, and a single stranded 3' terminal region capable of hybridizing to the antisense, complementary RNA sequence;
   (c) hybridizing the single stranded 3' terminal region of the nucleic acid sequence to the antisense, complementary RNA sequence;
   (d) ligating 5' end of the double stranded region of the nucleic acid sequence to 3' end of the antisense, complementary RNA sequence acid to form a second ligated sequence; and
   (e) transcribing the second ligated sequence with RNA polymerase to form amplified RNA sequences having the same sense as the target RNA sequence.

17. The methods of claim 15, wherein the nucleic acid sequences comprise DNA

18. The method of claim 15, wherein recessed 5' end of the nucleic acid sequences is phosphorylated and the terminal single stranded 3' end is blocked with a dideoxy extension blocker.

19. The method of claim 15, wherein the single stranded 3' terminal region of the nucleic acid sequences is at least 3 nucleotides long.

20. The method of claim 15, wherein the double stranded region of the nucleic acid sequences is at least 14 nucleotide pairs long.

21. The method of claim 15, wherein the ligation of step is carried out enzymatically.

22. The method of claim 15, wherein the RNA polymerase is a DNA-dependent RNA polymerase.

23. The method of claim 22, wherein the DNA-dependent RNA polymerase is a T7 RNA polymerase.

24. The method of claim 21, wherein the enzyme is a DNA ligase.

25. The method of claim 24, wherein the DNA ligase is a NAD+ dependent.

* * * * *

UNITED STATES PATENT AND TRADEMARK OFFICE
CERTIFICATE OF CORRECTION

PATENT NO. : 7,727,722 B2
APPLICATION NO. : 11/620804
DATED : June 1, 2010
INVENTOR(S) : Nelson et al.

It is certified that error appears in the above-identified patent and that said Letters Patent is hereby corrected as shown below:

In Column 5, Line 22, delete "phosphotase)." and insert -- phosphatase). --, therefor.

In Column 5, Line 32, before "used", delete "A" and insert -- As --, therefor.

In Column 6, Line 7, delete "enzyme-activable" and insert -- enzyme-activatable --, therefor.

In Column 6, Line 57, delete "my" and insert -- may --, therefor.

In Column 14, Line 19, delete "PT7IVSI5" and insert -- PT7IVS15 --, therefor.

In Column 14, Line 33, delete "cPT7IVSI5" and insert -- cPT7IVS15 --, therefor.

In Column 17, Line 1, delete "cPT7IVSI5" and insert -- cPT7IVS15 --, therefor.

In Column 29, Line 13, in Claim 3, delete "methods" and insert -- method --, therefor.

In Column 29, Line 16, in Claim 4, delete "methods" and insert -- method --, therefor.

In Column 29, Line 31, in Claim 10, delete "nucleotides" and insert -- nucleotides. --, therefor.

In Column 30, Line 28, in Claim 17, delete "methods" and insert -- method --, therefor.

In Column 30, Line 29, in Claim 17, delete "DNA" and insert -- DNA. --, therefor.

In Column 30, Line 49, in Claim 25, delete "dependent." and insert -- dependent ligase. --, therefor.

Signed and Sealed this

Seventeenth Day of August, 2010

David J. Kappos
*Director of the United States Patent and Trademark Office*